US012397064B2

(12) United States Patent
Tapparel Vu et al.

(10) Patent No.: US 12,397,064 B2
(45) Date of Patent: Aug. 26, 2025

(54) VIRUCIDAL NANOPARTICLES AND USE THEREOF AGAINST INFLUENZA VIRUS

(71) Applicant: ECOLE POLYTECHNIQUE FEDERALE DE LAUSANNE (EPFL), Lausanne (CH)

(72) Inventors: Caroline Tapparel Vu, Chêne-Bougeries (CH); Valeria Cagno, Vinzel (CH); Özgün Kocabiyik, Cambridge, MA (US); Francesco Stellacci, Morges (CH)

(73) Assignee: ECOLE POLYTECHNIQUE FEDERALE DE LAUSANNE, (EPFL) Lausanne (CH)

( * ) Notice: Subject to any disclaimer, the term of this patent is extended or adjusted under 35 U.S.C. 154(b) by 0 days.

(21) Appl. No.: 18/529,587

(22) Filed: Dec. 5, 2023

(65) Prior Publication Data

US 2024/0261431 A1 Aug. 8, 2024

Related U.S. Application Data

(63) Continuation of application No. 17/273,113, filed as application No. PCT/EP2019/073459 on Sep. 3, 2019, now abandoned.

(30) Foreign Application Priority Data

Sep. 4, 2018 (EP) .................................... 18192559

(51) Int. Cl.
*A61K 47/69* (2017.01)
*A61K 47/61* (2017.01)
*A61P 31/16* (2006.01)

(52) U.S. Cl.
CPC .......... *A61K 47/6939* (2017.08); *A61K 47/61* (2017.08); *A61P 31/16* (2018.01)

(58) Field of Classification Search
CPC ............ A61K 47/6939; A61K 47/6951; A61K 47/61; A61K 47/6929
See application file for complete search history.

(56) References Cited

U.S. PATENT DOCUMENTS

| | | | |
|---|---|---|---|
| 3,773,919 | A | 11/1973 | Boswell et al. |
| 5,134,127 | A | 7/1992 | Stella |
| 5,221,669 | A | 6/1993 | Anand |
| 5,248,675 | A | 9/1993 | Kurita |
| 6,165,995 | A | 12/2000 | Hilgers |
| 6,821,958 | B1 | 11/2004 | Hershline |
| 6,835,717 | B2 | 12/2004 | Hildreth |
| 9,364,618 | B2 | 6/2016 | Blacker et al. |
| 2002/0128227 | A1 | 9/2002 | Hildreth |
| 2003/0220294 | A1 | 11/2003 | Wallace |
| 2005/0209189 | A1 | 9/2005 | Hershline |
| 2008/0242636 | A1 | 10/2008 | Songok |
| 2010/0168366 | A1 | 7/2010 | Usui |
| 2013/0150312 | A1 | 6/2013 | Brown et al. |
| 2013/0231474 | A1 | 9/2013 | Auzely |
| 2014/0046061 | A1 | 2/2014 | Matos |
| 2014/0135477 | A1 | 5/2014 | Bovin |
| 2016/0058873 | A1 | 3/2016 | Fetzer et al. |
| 2016/0326270 | A1 | 11/2016 | Hong |
| 2016/0346382 | A1 | 12/2016 | Bryce |
| 2018/0050056 | A1 | 2/2018 | Kwak |
| 2019/0275073 | A1 | 9/2019 | Jones |
| 2020/0166506 | A1 | 5/2020 | Miyahara et al. |
| 2021/0137966 | A1 | 5/2021 | Jones |
| 2021/0154323 | A1 | 5/2021 | Aprikyan et al. |
| 2021/0322568 | A1 | 10/2021 | Tapparel Vu |
| 2022/0133905 | A1 | 5/2022 | Hawthorne et al. |
| 2023/0099027 | A1 | 3/2023 | Stellacci |
| 2023/0165891 | A1 | 6/2023 | Gasbarri et al. |

FOREIGN PATENT DOCUMENTS

| | | | |
|---|---|---|---|
| CN | 1747970 | A | 3/2006 |
| CN | 101362807 | | 2/2009 |
| CN | 101511385 | | 8/2009 |
| CN | 102282160 | A | 12/2011 |
| CN | 102382210 | | 3/2012 |
| CN | 109562125 | A | 4/2019 |
| EP | 0447171 | | 9/1991 |
| EP | 0506048 | | 9/1992 |
| EP | 0532026 | | 3/1993 |
| EP | 0606882 | | 7/1994 |
| EP | 3517117 | A1 | 7/2019 |
| FR | 2669535 | | 5/1992 |
| JP | H05139980 | | 6/1993 |
| JP | 2009001805 | A | 1/2009 |
| KR | 20090111328 | A | 10/2009 |
| WO | 1990000596 | | 1/1990 |
| WO | 1992003453 | | 3/1992 |
| WO | 1992012709 | | 8/1992 |
| WO | 2002055562 | | 7/2002 |
| WO | 2003057176 | | 7/2003 |

(Continued)

OTHER PUBLICATIONS

Apretude (cabotegravir extended-release injectable suspension), Highlights of Prescribing Information, Manufactured for: ViiV Healthcare, 48 pages, (issued: Dec. 2021).

Bhatia, S. et al., "Linear polysialoside outperforms dendritic analogs for inhibition of influenza virus infection in vitro and in vivo", Biomaterials, 138:22-34, (2017).

De Clercq, E., "Selective virus inhibitors", Microbiologica., 13(2):165-78, (1990).

Debouzy, J. et al., "Substituted cyclodextrins as chelating reagents for ethers, thioethers and yperite", Ann Pharm Fr., 58(1):20-3, (2000).

Galus, A. et al., "Hexagonal-shaped chondroitin sulfate self-assemblies have exalted anti-HSV-2 activity", Carbohydrate Polymers, 136:113-120, (2016).

(Continued)

*Primary Examiner* — James W Rogers
(74) *Attorney, Agent, or Firm* — Weaver Austin Villeneuve & Sampson LLP

(57) ABSTRACT

The invention relates to virucidal nanoparticles comprising a trisaccharide moiety and use thereof against influenza virus.

12 Claims, 20 Drawing Sheets

(56) References Cited

FOREIGN PATENT DOCUMENTS

| WO | 2004069873 | 8/2004 |
|---|---|---|
| WO | 2005042584 | 5/2005 |
| WO | 2006003521 | 1/2006 |
| WO | 2008087034 | 7/2008 |
| WO | 2009001805 | 12/2008 |
| WO | 2010043230 | 4/2010 |
| WO | WO-2010080819 A1 | 7/2010 |
| WO | 2011151667 | 12/2011 |
| WO | 2013172725 | 11/2013 |
| WO | 2015179963 | 12/2015 |
| WO | WO-2016166317 A1 | 10/2016 |
| WO | 2018015465 | 1/2018 |
| WO | 2018199179 | 11/2018 |
| WO | 2020048976 | 3/2020 |
| WO | 2021198139 | 10/2021 |

OTHER PUBLICATIONS

Gambaryan, A. et al., "Polymer-bound 6' sialyl-N-acetyl-lactosamine protects mice infected by influenza virus", Antiviral Res., 68(3):116-23, (2005).
International Application No. PCT/EP2017/068291; International Preliminary Report on Patentability, date of issuance Jan. 22, 2019; 8 pages.
International Application No. PCT/EP2017/068291; International Search Report and Written Opinion of the International Searching Authority, date of mailing Oct. 26, 2017; 14 pages.
International Application No. PCT/EP2019/073459; International Preliminary Report on Patentability, date of issuance Mar. 9, 2021; 10 pages.
International Application No. PCT/EP2019/073459; International Search Report and Written Opinion of the International Searching Authority, date of mailing Dec. 4, 2019; 14 pages.
International Application No. PCT/EP2021/058086; International Preliminary Report on Patentability, date of issuance Sep. 29, 2022; 8 pages.
International Application No. PCT/EP2021/058086; International Search Report and Written Opinion of the International Searching Authority, date of mailing, Jun. 10, 2021; 11 pages.
International Application No. PCT/US2022/080538; International Search Report and Written Opinion of the International Searching Authority, date of mailing, Mar. 30, 2023; 9 pages.
Jones, S. et al., "Modified cyclodextrins as broad-spectrum antivirals", Sci Adv., 6(5):eaax9318, (2020).
Kirschner, D. et al., "Fine tuning of sulfoalkylated cyclodextrin structures to improve their mass-transfer properties in an aqueous biphasic hydroformylation reaction", J Mol Catalysis A, 286(1-2):11-20, (2008).
Kocabiyik, O. et al., "Non-Toxic Virucidal Macromolecules Show High Efficacy Against Influenza Virus Ex Vivo and In Vivo", Adv Sci (Weinh)., 8(3):2001012, (2020).
Kocabiyik, O., "Virucidal Nanomaterials Against Influenza", Thesis No. 1234, 111 pages, (2018).
Liang, S. et al., "Synthesis and structure-activity relationship studies of water-soluble b-cyclodextrin-glycyrrhetinic acid conjugates as potential anti-influenza virus agents", Eur J Med Chem., 166:328-38, (2019).
Nagase, Y. et al., "Protective effect of sulfobutyl ether beta-cyclodextrin on DY-9760e-induced hemolysis in vitro", J Pharm Sci., 91(11):2382-9, (2002).
Oh, D. et al., "Using the Ferret as an Animal Model for Investigating Influenza Antiviral Effectiveness", Front Microbiol., 7(80):1-12, (2016).
Papp, I. et al., "Inhibition of influenza virus infection by multivalent sialic-acid-functionalized gold nanoparticles", Small, 6(24):2900-6, (2010).
Pauwels, R. et al., "Development of vaginal microbicides for the prevention of heterosexual transmission of HIV", J Acquir Immune Defic Syndr Hum Retrovirol., 11(3):211-21, (1996).

Sallas, F. et al., "Amphiphilic Cyclodextrins—Advances in Synthesis and Supramolecular Chemistry", Eur J Organic Chem., 2008(6):957-69, (2008).
Schols, D. et al., "Sulphated cyclodextrins are potent anti-HIV agents acting synergistically with 2' , 3' deoxynucleoside analogues", Antiviral Chem & Chemo., 2(1):45-53, (1991).
Shityakov, S. et al., "Sevoflurane-sulfobutylether-β-cyclodextrin complex: Preparation, characterization, cellular toxicity, molecular modeling and blood-brain barrier transport studies", Molecules, 20(6):10264-79, (2015).
Tamiflu® (oseltamivir phosphate) capsules, Highlights for Prescribing Information, Distributed by: Genentech, Inc., 29 pages, (revised: Aug. 2019).
The Merck Manual, 16th Ed., pp. 183-189, (1992).
Tian, Z. et al., "Inhibition of influenza virus infection by multivalent pentacyclic triterpene-functionalized per-O-methylated cyclodextrin conjugates", Eur J Med Chem., 134:133-9, (2017).
Tuzikov, A. et al., "Conversion of complex sialooligosaccharides into polymeric conjugates and their anti-influenza virus inhibitory potency", J Carb Chem., 19(9):1191-1200, (2000).
U.S. Appl. No. 17/155,482; Applicant-Initiated Interview Summary, dated Nov. 28, 2022; 11 pages.
U.S. Appl. No. 17/155,482; Final Office Action, dated Jan. 22, 2023; 24 pages.
U.S. Appl. No. 17/155,482; Final Office Action, dated Oct. 5, 2023; 21 pages.
U.S. Appl. No. 17/155,482; Non-Final Office Action, dated Aug. 26, 2022; 22 pages.
U.S. Appl. No. 17/273,113; Final Office Action, dated Sep. 6, 2023; 15 pages.
Urbinati, C. et al., "Polyanionic drugs and viral oncogenesis: a novel approach to control infection, tumor-associated inflammation and angiogenesis", Molecules, 13(11):2758-85, (2008).
US Public Health Service, "Preexposure Prophylaxis for the Prevention of HIV Infection in the United States—2021 Update: A Clinical Practice Guideline", Centers for Disease Control and Prevention, 108 pages, (2021).
Witvrouw, M. et al., "Sulfated polysaccharides extracted from sea algae as potential antiviral drugs", Gen Pharmacol., 29(4):497-511, (abstract only), (1997).
Xiao, S. et al., "Pentacyclic triterpenes grafted on CD cores to interfere with influenza virus entry: A dramatic multivalent effect", Biomaterials, 78:74-85, (2016).
XOFLUZAR (baloxavir marboxil) tablets, Highlights of Prescribing Information, Distributed by: Genentech, USA, Inc., 22 pages, (revised: Aug. 2022).
Yamazaki, N. et al., "Synthesis, lectin-binding affinity, and biodistribution of novel neoglycoprotein-liposome conjugates bearing 6'-sialyl-N-acetyllactosamines and Lewis x trisaccharides", Drug Deliv Sy., 14(6):498-505, (1999).
Zhang, P. et al., "Clustering of PK-trisaccharides on amphiphilic cyclodextrin reveals unprecedented affinity for the Shiga-like toxin Stx2", Chem Commun (Camb.), 53(76):10528-31, (2017).
De Clercq E., "Selective Virus Inhibitors," Medline, US National Library of Medicine (NLM), Bethesda, MD, US, Database Accession No. NLM1693749, Apr. 1990, XP002774104.
International Preliminary Report on Patentability and Written Opinion dated Apr. 4, 2024 in PCT Application No. PCT/US2022/076753.
International Preliminary Report on Patentability and Written Opinion dated Feb. 9, 2023 in PCT Application No. PCT/EP2021/070990.
International Preliminary Report on Patentability and Written Opinion dated Feb. 9, 2023 in PCT Application No. PCT/EP2021/071188.
International Search Report and Written Opinion dated Jan. 5, 2023 in PCT Application No. PCT/US2022/76753.
International Search Report and Written Opinion dated Mar. 18, 2024 in PCT Application No. PCT/US2023/076947.
International Search Report and Written Opinion dated Nov. 3, 2021 in PCT Application No. PCT/EP2021/071188.
International Search Report and Written Opinion dated Oct. 28, 2021 in PCT Application No. PCT/EP2021/070990.

(56) References Cited

OTHER PUBLICATIONS

U.S. Final Office Action dated Sep. 2, 2020 in U.S. Appl. No. 16/319,009.
U.S. Non-Final Office Action dated Apr. 21, 2023 in U.S. Appl. No. 17/273,113.
U.S. Non-Final Office Action dated Apr. 28, 2023 in U.S. Appl. No. 17/155,482.
U.S. Non-Final Office Action dated May 13, 2020 in U.S. Appl. No. 16/319,009.
U.S. Restriction Requirement dated Feb. 15, 2023 in U.S. Appl. No. 17/273,113.
U.S. Restriction Requirement dated Mar. 6, 2020 in U.S. Appl. No. 16/319,009.

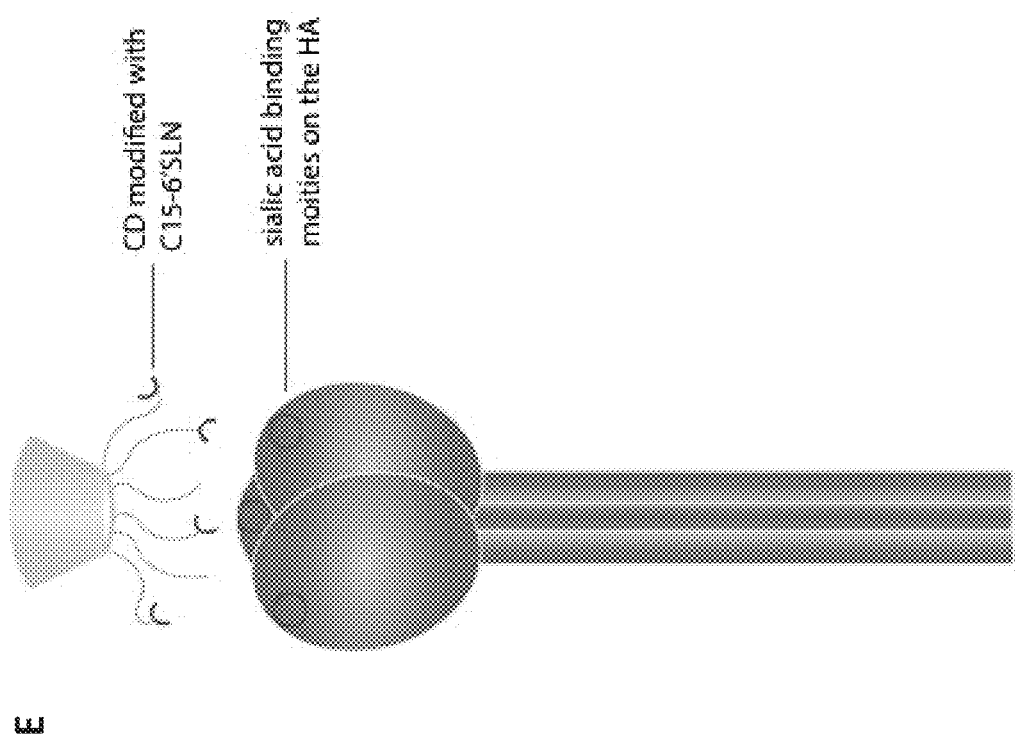

Figure 4
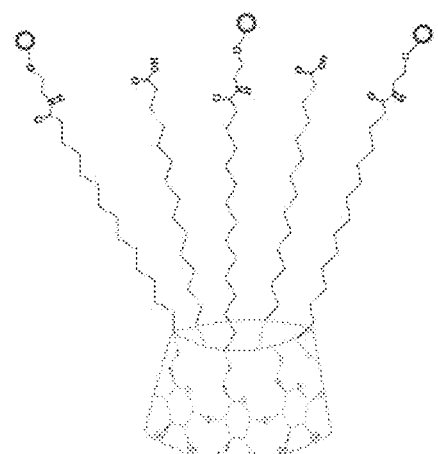
C14-6'
6'SLN/β-CD: 3
EC$_{50}$: 0.8 (0.4-1.4) μg/mL
Activity: Virucidal
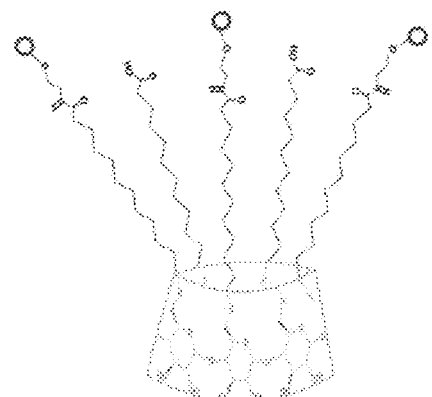
C11-6'
6'SLN/β-CD: 3.1
EC$_{50}$: 0.18 (0.14-0.24) μg/mL
Activity: Virucidal
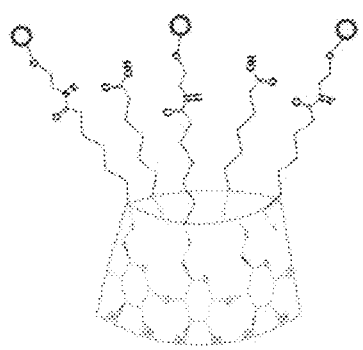
C6-6'
6'SLN/β-CD: 2.7
EC$_{50}$: 0.3 (0.23-0.38) μg/mL
Activity: Virucidal
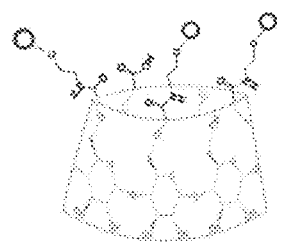
C1-6'
6'SLN/β-CD: 3
EC$_{50}$ > 100 μg/mL
Activity: N/A Figure 4 cont.
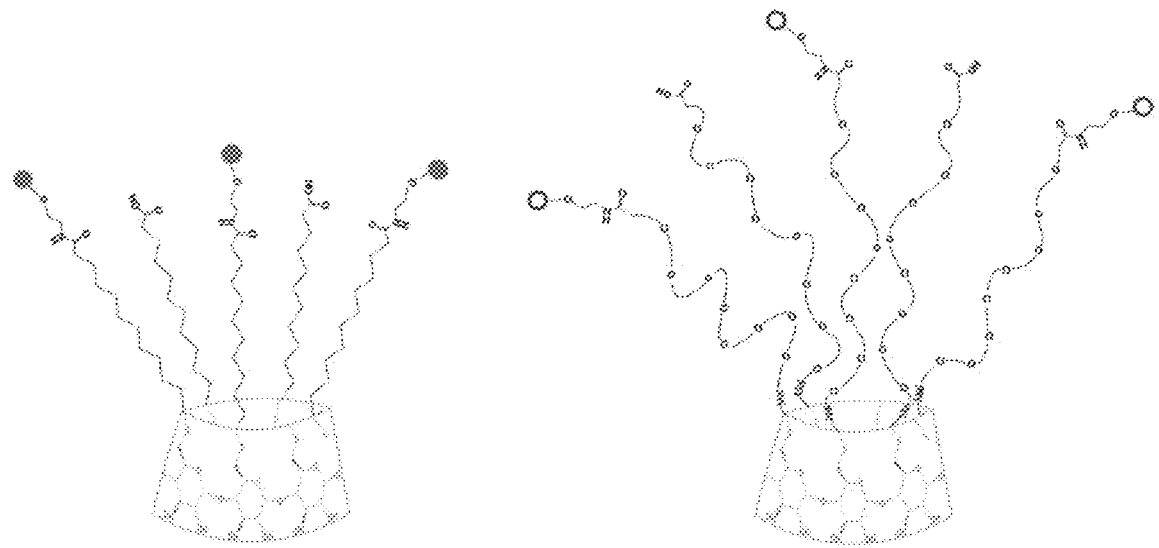
C11-3'
3'SLN/β-CD: 2.7
EC$_{50}$: 6.5 (4.1-10.1) µg/mL
Activity: Virucidal
P8-6'
6'SLN/β-CD: 3.5
EC$_{50}$: 4.9 (3.6-6.5) µg/mL
Activity: Virustatic
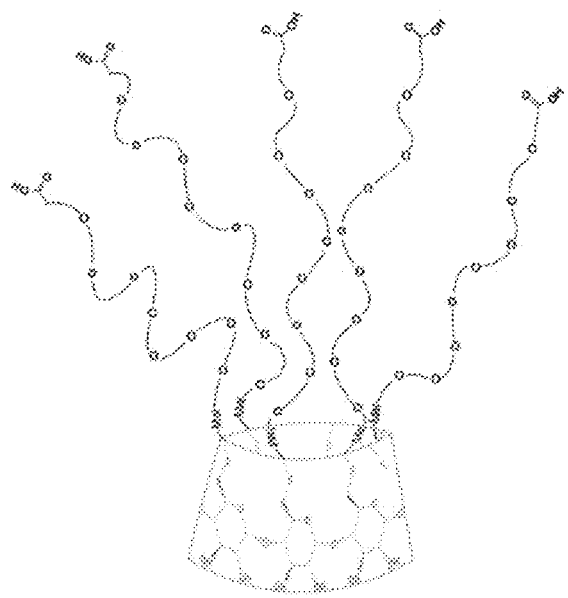
P8
6'SLN/β-CD: -
EC$_{50}$ > 500 µg/mL
Activity: N/A Figure 18
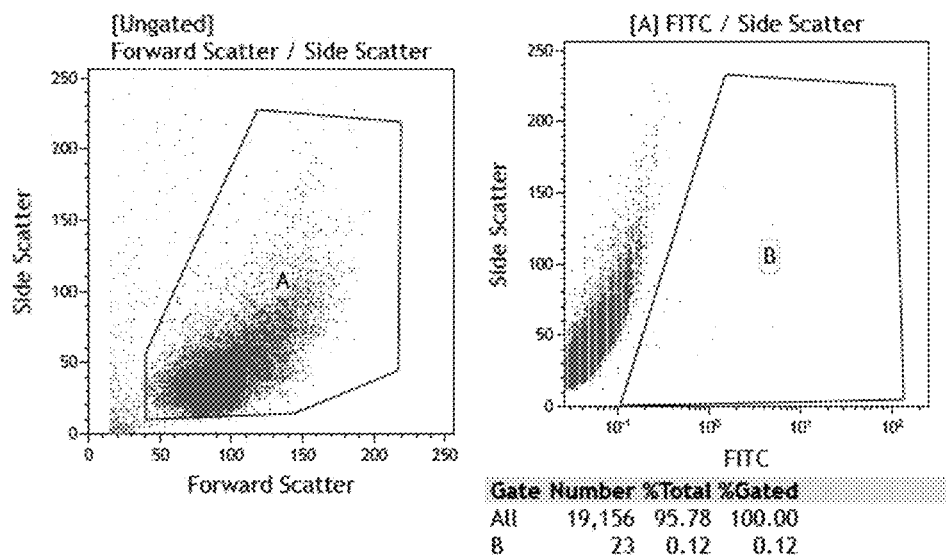
Positive control (Infection No CDs)
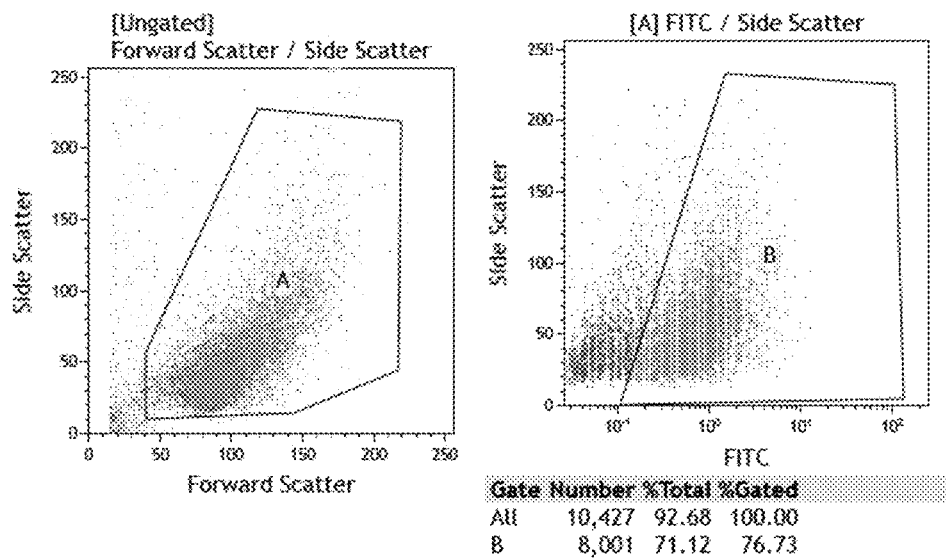

VIRUCIDAL NANOPARTICLES AND USE THEREOF AGAINST INFLUENZA VIRUS

FIELD OF THE INVENTION

The invention relates to virucidal nanoparticles comprising a trisaccharide moiety and the use thereof against influenza virus.

BACKGROUND OF THE INVENTION

Influenza viruses are among the most infective viruses. Every year different influenza strains infect a large fraction of both the animal and human population, endangering infants, the elderly and immunocompromised people, all having a risk of hospitalization and death due to influenza-related complications. As a result, seasonal influenza poses remarkable impacts on socio-economy. In fact, respiratory diseases can cost a significant fraction of the total health expenditures in developed and mainly in developing countries. Because influenza mutates so rapidly, the development of a vaccine is still a major challenge. Vaccine development would pose even higher challenges when focused on the occasional pandemics instead of yearly outbreaks. In such case, the development time of a new vaccine, which is on average 6 months, would represent a serious risk. Furthermore, even in the presence of a vaccine, reaching a reasonable vaccination coverage is far from a foregone conclusion. Therefore, the risk of a new pandemic, such as the Spanish-flu, is still present and recognised as one of the top threats to global health.

Naturally, the second line of defence after vaccines, are antiviral drugs. A number of anti-influenza drugs are currently approved: neuraminidase inhibitors such as zanamivir and oseltamivir, ion channel inhibitors such as amantadine, fusion inhibitors such as umifenovir (only in Russia and China) and polymerase inhibitor such as baloxavir marboxil, which was recently approved in US and Japan. Yet, it is recognized that the efficacy of current drugs is far from ideal. Concerns about these drugs range from significant side effects to the appearance of drug-resistant viruses after a short period of use. Given the importance of this issue, a number of other drugs are in clinical trials. The majority of these drugs are monoclonal antibodies that inhibit the fusion of the virus to the host-cell. Although they are promising, it is likely that they will be considerably costly due to their manufacturing processes.

There are quite a few research lines on the development of molecules that target conserved parts of the virus. Further, the search for virucidal (i.e. irreversible) drugs with limited toxicity has been very challenging. Recently, it was found that peptides isolated from the frog skin have such property, but their $EC_{50}$ is only micromolar and their toxicity is arguable.

The interaction between the viral hemagglutinin (HA) and the sialic acid (SA)-bearing glycoproteins on host-cells is the primary step of influenza infection. The binding affinity between the SA and HA is low and compensated for by multivalent binding. Inspired by this natural phenomenon, there have been several attempts to inhibit influenza virus using SA coated multivalent materials such as polymers, dendrimers and nanoparticles.

Reuter et al. synthesized sialic acid decorated polymeric materials in various architectures such as linear polymers, comb-branched polymers and dendrons; tested them against different strains of influenza A virus. Only high molecular weight (>100 kDa) branched architectures were found to be inhibiting one strain of influenza virus, X-31, at micromolar concentrations of sialic acid. Papp et al. tested inhibition activity of sialic acid functionalized gold nanoparticles (NPs) against influenza virus an X-31 strain and reported that NPs of 14 nm core diameter have better inhibition activity than 2 nm NPs. However, in this study they did not mention the NP concentrations to inhibit the virus. The same group also synthesized sialic acid decorated glycoarchitectures of different sizes and inhibited X-31 strain at millimolar concentrations.

It was known that human influenza virus preferentially binds α2,6-linked SA on the glycoproteins. More recently, multivalent materials bearing α2,6-sialyllactose were demonstrated to inhibit influenza virus at low micromolar concentrations. Tang et al. synthesized brush polymers bearing α2,6-sialyllactose which inhibited influenza A PR8 strain at micromolar concentrations of sialic acid unit. Kwon et al. decorated PAMAM dendrimers with α2,6-sialyllactose and inhibited several strains of influenza such as influenza A PR8, CAL 09 and NWS 33.

Micromolar material concentrations to inhibit the influenza virus in vitro are still too high and in vivo concentrations will be even higher. Also, most of the entry inhibitors are virustatic; the virus becomes infective again upon dilution of virus-material complex in vitro. In the absence of a wide spectrum effective vaccine, there is an unmet need for drugs against influenza. An ideal anti-influenza drug should be broad-spectrum, target a highly conserved part of the virus, have an irreversible effect, i.e. be virucidal (in order to avoid loss of efficacy due to the dilution in body fluids) at low concentrations, and obviously be non-toxic.

SUMMARY OF THE INVENTION

To address this problem, the present invention provides nanoparticles that strongly interact with the HA, irreversibly inhibit the infectivity of influenza virus at low concentrations, and display exceedingly-low toxicity.

An aspect of the present invention provides a virucidal nanoparticle comprising a core and a plurality of ligands covalently linked to the core, wherein at least a portion of said ligands comprise a trisaccharide moiety and wherein:

the core is cyclodextrin, the ligands are the same or different and are optionally substituted alkyl-based ligands, and each trisaccharide moiety is selected from 3-sialyl-N-acetyllactosamine (3'SLN) and 6-sialyl-N-acetyllactosamine (6'SLN).

Another aspect of the present invention provides a virucidal nanoparticle represented by Formula (I)

$$\text{Cyclodextrin} - S \underset{n}{\overbrace{\phantom{xxx}}} \overset{O}{\underset{H}{\overbrace{N}}} \sim O \sim \text{Trisaccharide moiety} \bigg]_m \quad (I)$$

wherein m is 2 to 8, and n is 2 to 28 or 4 to 13.

Another aspect of the present invention provides a virucidal nanoparticle represented by Formula (II)

$$\left[ \begin{array}{c} R' \quad R' \\ O \quad O \\ \diagup \diagdown \\ \diagdown \diagup O \\ O \\ \diagup \\ R \end{array} \right]_x \quad (II)$$

wherein:
each R, independently, is an optionally substituted alkyl-based ligand, wherein at least two of said ligands have a trisaccharide moiety selected from the group comprising 3-sialyl-N-acetyllactosamine (3'SLN) and 6-sialyl-N-acetyllactosamine (6'SLN), or wherein at least one of said ligands has 3'SLN and another has 6'SLN;
each R', independently, is H, —(CH$_2$)$_y$—COOH, —(CH$_2$)$_y$—SO$_3$$^-$, a polymer or a water solubilizing moiety;
x is 6, 7 or 8; and
y is an integer from 4 to 20,
or a pharmaceutically acceptable salt thereof.

A further aspect of the present invention provides a pharmaceutical composition comprising an effective amount of one or more virucidal nanoparticles of the present invention and at least one pharmaceutically acceptable excipient, carrier and/or diluent.

A further aspect of the present invention provides the virucidal nanoparticle of the present invention for use in treating and/or preventing influenza virus infections and/or diseases associated with influenza viruses.

A further aspect of the present invention provides a virucidal composition comprising an effective amount of one or more virucidal nanoparticles of the present invention and optionally at least one suitable aerosol carrier.

A further aspect of the present invention provides a method of disinfection and/or sterilization comprising using the virucidal compositions of the present invention, or a virucidal nanoparticle of the present invention.

A further aspect of the present invention provides a device comprising the virucidal compositions of the present invention, or one or more virucidal nanoparticles of the present invention and means for applying or dispensing the virucidal compositions or the virucidal nanoparticles.

A further aspect of the present invention provides a use of the virucidal nanoparticles of the present invention or the virucidal compositions of the present inventions for sterilization and/or for disinfection.

BRIEF DESCRIPTION OF FIGURES

FIG. 4 shows exemplary modified cyclodextrins. Number of 6'SLN or 3'SLN per β-CD is the average number calculated by $^1$H NMR. The representative chemical structures of modified cyclodextrins were constructed based on NMR results. EC$_{50}$ represents the half-inhibitory concentrations on MDCK cells at 24 hpi against A/Netherlands/2009 (H1N1) (FIG. 7). N/A: not assessable. For ease of reference in these 3D structures, some of the rearward cyclodextrin sugars, ligands and trisaccharides are not shown.

In FIG. 11(b) immunofluorescence at 7 days post-infection (co-treatment condition) confirms the protection provided by C11-6'. Red: monoclonal antibody Influenza A, blue: DAPI, green: β-IV-tubulin (marker of ciliated cells). The thickness of each tissue was demonstrated at the bottom of the corresponding image (b). C11-6' also showed high efficacy in post-treatment condition (c). Results of (a) and (c) are mean and SEM of 2 to 4 independent experiments performed in duplicate. Images of (b) are representative of 10 images taken for each condition.

FIG. 18 shows the gating strategy performed for FACS.

DETAILED DESCRIPTION OF THE INVENTION

Figure 1:
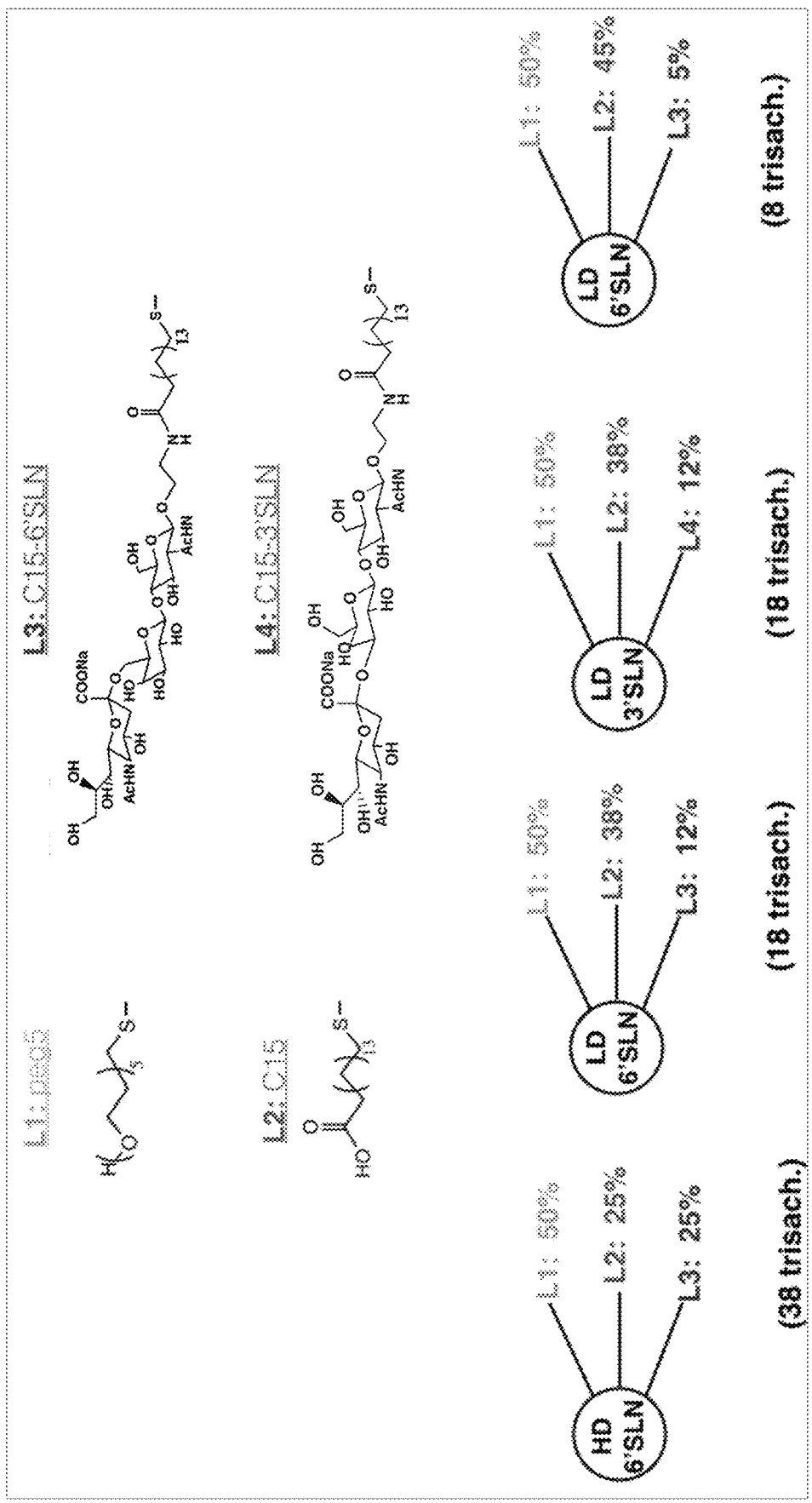
FIG. 1 shows chemical structure of NPs with different ligand composition. Average NP diameter: 2.9±0.9 nm.

All publications, patent applications, patents, and other references mentioned herein are incorporated by reference in their entirety. The publications and applications discussed herein are provided solely for their disclosure prior to the filing date of the present application. Nothing herein is to be construed as an admission that the present invention is not entitled to antedate such publication by virtue of prior invention. In addition, the materials, methods, and examples are illustrative only and are not intended to be limiting.

In the case of conflict, the present specification, including definitions, will control. Unless defined otherwise, all technical and scientific terms used herein have the same meaning as is commonly understood by one of skill in art to which the subject matter herein belongs. As used herein, the following definitions are supplied in order to facilitate the understanding of the present invention.

The term "comprise" is generally used in the sense of include, that is to say permitting the presence of one or more features or components. In addition, as used in the specification and claims, the language "comprising" can include analogous embodiments described in terms of "consisting of" and/or "consisting essentially of".

As used in the specification and claims, the term "and/or" used in a phrase such as "A and/or B" herein is intended to include "A and B", "A or B", "A", and "B".

As used in the specification and claims, the singular forms "a", "an" and "the" include plural references unless the context clearly dictates otherwise.

As used in the specification and claims, the term "at least one" used in a phrase such as "at least one C atom" can mean "one C atom" or "two C atoms" or more C atoms.

As used herein, the term "virustatic" refers to a characterization of antiviral efficacy determined by in vitro testing demonstrating reversible inhibition of the infectivity of a virus following interaction with an antiviral composition. The interaction inhibits infectivity, for example, by binding to the virus or otherwise interfering with the virus' surface ligands. However, once the interaction terminates (for example, by dilution) and in the absence of any added materials or conditions promoting viral reconstitution, it is possible for the virus to resume infectivity.

As used herein, the term "virucidal" refers to a characterization of antiviral efficacy determined by in vitro testing demonstrating irreversible inhibition of the infectivity of a virus following interaction with an antiviral compound or composition. The interaction inhibits infectivity, for example, by binding to the virus or otherwise interfering with the virus' surface ligands. However, even following termination of the interaction (for example, by dilution) and in the absence of any added materials or conditions promoting viral reconstitution, it is essentially impossible for the virus to resume infectivity.

As used herein, the term "biocompatible" refers to compatibility with living cells, tissues, organs, or systems, and having no significant risk of injury, toxicity, or rejection by the immune system.

As used herein, "nano", such as used in "nanoparticle", refers to nanometric size, such as a particle having a nanometric size, and is not intended to convey any specific shape limitation. In particular, "nanoparticle" encompasses nanospheres, nanotubes, nanoboxes, nanoclusters, nanorods and the like. In certain embodiments the nanoparticles and/or nanoparticle cores contemplated herein have a generally polyhedral or spherical geometry.

As used herein, "influenza" refers to sialic acid-seeking, airborne transmissible (human or animal) RNA viruses, such as influenza A virus, influenza B virus, influenza C virus and influenza D virus. Influenza A virus encompasses the following serotypes: H1N1, H2N2, H3N2, H5N1, H7N7, H1N2, H9N2, H7N2, H7N3, H10N7, H7N9, and H6N1.

As used herein, the term "alkyl" refers to a straight hydrocarbon chain containing from 1 to 50 carbon atoms, preferably 4 to 30 carbon atoms. Representative examples of alkyl include, but are not limited to, methyl, ethyl, propyl, butyl, pentyl, hexyl, heptyl, octyl, nonyl, decyl, . . . .

As used herein, the term "carboxyalkyl" refers to a carboxy group appended to the parent molecular moiety through an alkyl group as defined herein.

While α2,6-linked sialic acids have been known to interact with human influenza virus, the exact glycan sequence providing high affinity binding has remained unclear in the literature. The present inventors have demonstrated that a majority of human influenza viruses bind with high affinity to glycans that terminate with two or more, preferably three or four trisaccharide moieties, specifically 6-sialyl-N-acetyl-lactosamine (6'SLN) or 3-sialyl-N-acetyllactosamine (3'SLN).

An aspect of the present invention provides a virucidal nanoparticle comprising a core and a plurality of ligands covalently linked to the core, wherein at least a portion of said ligands comprise a trisaccharide moiety and wherein the core is metal nanoparticle or organic material, wherein preferably the metal nanoparticle is selected from the group comprising gold nanoparticles, iron oxide nanoparticles, silver nanoparticles, platinum nanoparticles, cobalt nanoparticles, zinc nanoparticles, silica nanoparticles, cadmium selenide nanoparticles, gold-silver alloy nanoparticles, aluminium oxide nanoparticles, copper oxide nanoparticles, magnesium oxide nanoparticles, nickel oxide nanoparticles, titanium dioxide nanoparticles, zinc oxide nanoparticles, and more preferably the metal nanoparticle is a gold nanoparticle, and wherein organic material is selected from the group comprising cyclodextrins, polymers, dendrimers, and dendrons, preferably the organic material is a cyclodextrin, the ligands are the same or different and are optionally substituted alkyl-based ligands or polyethylene glycol (PEG) based ligands. Preferably the optionally substituted alkyl-based ligands are optionally substituted $C_4$-$C_{30}$ alkyl-based ligands, more preferably the optionally substituted alkyl-based ligands are optionally substituted $C_4$-$C_{30}$ carboxyalkyls; preferably PEG-based ligands are selected from the group comprising $PEG_3$, $PEG_4$, $PEG_5$, $PEG_6$, $PEG_7$, $PEG_8$; more preferably the ligands are derived from the group comprising polyethylene glycol 5 ($PEG_5$), 16-mercaptohexadeconic acid (C15), and 11-mercaptoundecanoic acid, the trisaccharide moiety is 3-Sialyl-N-acetyllactosamine (3'SLN) and/or 6-Sialyl-N-acetyllactoseamine (6'SLN).

In the context of the present invention, the trisaccharide moiety is exposed on a ligand covalently bound to the outer surface of a nanoparticle (NP) in a manner so that any other ligands do not hinder the interaction between the trisaccharide moiety and the influenza virus.

The mean diameter of the core ranges from about 1.0 nm to about 200 nm, preferably from 1 nm to 5 nm, most preferably from 1.5 nm to 3 nm. The overall nanoparticle size has a mean particle diameter of from 3 nm to 250 nm, or from 3 nm to 200 nm, preferably from 3 nm to 10 nm, more preferably from 4.5 nm to 6 nm.

In some embodiments, the core in virucidal nanoparticles of the invention is organic material, preferably a polymer, wherein a polymer is selected from the group comprising polyacrylic acid (PAA), polyvinyl alcohol (PVA), polyethylene glycol (PEG), polylactic acid (PLA), polyglycolide (PGA), polydioxanone (PDO), and poly(lactic-co-glycolic acid).

In some embodiments, the core in virucidal nanoparticles of the invention is organic material, preferably a dendrimer selected from the group comprising poly(amidoamine) (PAMAM) and bis-MPA.

In some embodiments, the core in virucidal nanoparticles of the invention is organic material, preferably a dendron selected from the group comprising poly(amidoamine) (PAMAM) and bis-MPA.

In preferred embodiments, the core in virucidal nanoparticles of the invention is organic material which is cyclodextrin.

Cyclodextrins (CDs) are naturally occurring cyclic glucose derivatives consisting of alpha(14)-linked glucopyranoside units. Their cyclic structure creates a truncated cone shape with the primary hydroxyls of the glucose units on the narrow face and the secondary hydroxyls on the wider face. Each face can be readily and independently functionalised. The most commonly used natural CDs have 6, 7, and 8 glucopyranoside units, referred to as alpha, beta and gamma cyclodextrin respectively. The preferred cyclodextrin is beta. Because of the cyclic structure of CDs, they have a cavity capable of forming supramolecular inclusion complexes with guest molecules. As CDs are naturally occurring, readily functionalised, have a cavity for guest inclusion and are biocompatible, they have found use in many commercial applications including drug delivery, air fresheners, etc. The difference in reactivity of each face of CDs has been used for the synthesis of a wide range of modified cyclodextrins. The primary face of CDs is more readily modified, with control over the degree and location of substitution being possible. CD derivatives that bear a good leaving group, such as halogenated CDs, are important intermediates in CD functionalisation. By replacing all of the primary hydroxyl units of CDs with iodo-units gives an intermediate that allows for complete functionalisation of the primary face, whilst leaving the secondary hydroxyls and the rigid truncated cone shape in tact. In one embodiment, heptakis-6-iodo-6-deoxy-beta-cyclodextrin was synthetized followed by reaction with mercaptoundecaosulphonate (MUS) to yield a CD functionalised on the primary face with undecanaosulfonate groups. It is then possible to independently modify the secondary face of the cyclodextrin to introduce further solubilising groups, dye molecules, polymers, etc. Moreover, the size of β-CD (d~1.5 nm) falls within the preferred nano size for cores of the invention and matches well with the HA globular head (~5 nm). Beta-cyclodextrin has a rigid chemical structure that is believed to contribute to virucidal activity, and can have maximum of 7 trisaccharide-bearing ligands depending from the narrow face, preferably 3 to 4 trisaccharide-bearing ligands, three being the number of sialic acid binding points in the influenza virus HA globular head.

The virucidal nanoparticles of the present invention can also be purified single molecules or compounds which are also intended to be encompassed within the scope of the present invention.

An embodiment of the present invention provides a virucidal nanoparticle comprising a core and a plurality of ligands covalently linked to the core, wherein at least a portion of said ligands comprise a trisaccharide moiety and wherein the core is cyclodextrin, preferably selected from the group comprising alpha-cyclodextrin, beta-cyclodextrin, gamma-cyclodextrin or combinations thereof, the ligands are the same or different and are optionally substituted alkyl-based ligands, preferably optionally substituted $C_4$-$C_{30}$ alkyl-based ligands, more preferably optionally substituted $C_6$-$C_{15}$ alkyl-based ligands, each trisaccharide moiety is selected from 3-sialyl-N-acetyllactoseamine (3'SLN) and 6-sialyl-N-acetyllactoseamine (6'SLN).

In some embodiments of the virucidal nanoparticles of the invention, some or all of the ligands comprise 3'SLN, some or all of said ligands comprise 6'SLN, and some but not all of said ligands comprise no trisaccharide moiety.

A virucidal nanoparticle of the present invention, wherein the core is cyclodextrin, can be represented by Formula (I)

(I)

[Cyclodextrin]—S—[CH$_2$)$_n$—C(O)—NH—CH$_2$CH$_2$—O—Trisaccharide moiety]$_m$ wherein
- m is 2 to 8, preferably m is 2 to 7 or 2 to 6, more preferably m is 3 or 4,
- n is 2 to 28 or 4 to 13 or 4 to 30 or 6 to 15, preferably 2 to 28 or 4 to 13, in some embodiments n is 2 or 4 or 6 to 13 or 28 or 30, and
- preferably cyclodextrin is selected from the group comprising alpha-cyclodextrin, beta-cyclodextrin, gamma-cyclodextrin or combinations thereof, Another aspect of the present invention provides a virucidal nanoparticle represented by Formula (II)

(II)

$$\left[\begin{array}{c} R' \quad R' \\ | \quad | \\ O \quad O \\ \diagdown \diagup \\ \text{(sugar ring)} \\ | \\ R \end{array}\right]_x$$

wherein
- each R, independently, is an optionally substituted alkyl-based ligand, wherein at least two of said ligands have a trisaccharide moiety selected from the group comprising 3-sialyl-N-acetyllactoseamine (3'SLN) and 6-sialyl-N-acetyllactoseamine (6'SLN), or wherein at least one of said ligands has 3'SLN and another has 6'SLN; preferably optionally substituted alkyl-based ligand is optionally substituted $C_4$-$C_{30}$ alkyl-based ligand, more preferably optionally substituted $C_6$-$C_{15}$ alkyl-based ligand or optionally substituted $C_6$-$C_{15}$ alkyl-based ligand comprising 6'SLN;
- each R', independently, is H, —(CH$_2$)$_y$—COOH, —(CH$_2$)$_y$—SO$_3$$^-$, a polymer or a water solubilizing moiety; preferably R' is H; preferably R', independently, is H, —(CH$_2$)$_y$—COOH, —(CH$_2$)$_y$—SO$_3$$^-$, or a polymer; preferably R', independently, is —(CH$_2$)$_y$—COOH, —(CH$_2$)$_y$—SO$_3$$^-$, or a polymer; preferably R', independently, is H, —(CH$_2$)$_y$—COOH, or —(CH$_2$)$_y$—SO$_3$$^-$; preferably R', independently, is —(CH$_2$)$_y$—COOH, or —(CH$_2$)$_y$—SO$_3$$^-$;
- x is 6, 7 or 8; and
- y is an integer from at least 4 to about 20, preferably y is at least 4, preferably y is 4 to 20, preferably y is 7 to 11, most preferably y is 10. In other embodiments, y is at least 6, at least 7, at least 8, at least 9, at least 10, at least 11. In other embodiments, y is at maximum 100, at maximum 70, at maximum 50, at maximum 25, at maximum 20, at maximum 15.
- or a pharmaceutically acceptable salt thereof.

The polymer in the virucidal nanoparticles of the invention can be selected from both synthetic and natural polymers. In an embodiment of the invention, the synthetic polymers are selected from the group comprising, but not limited to, poly(ethylene glycol) (PEG), poly(vinyl alcohol) (PVA), poly(acrylamide) (PAAm), poly(n-butyl acrylate), poly-(α-esters), (PEG-b-PPO-b-PEG), poly(N-isopropylacrylamide) (pNIPAAM), polylacticglycolic acid (PLGA) and/or combinations thereof.

In another embodiment of the invention, the natural polymers are selected from the group comprising dextran, dextrins, glucose, cellulose and/or combinations thereof.

In some embodiments of virucidal nanoparticles of the invention, the trisaccharide moiety is preferably 6'SLN, which is specific to human influenza strains. In other embodiments of virucidal nanoparticles of the invention, the trisaccharide moiety is preferably 3'SLN, which is specific to avian influenza strains.

The ligands (or ligand compounds) of virucidal nanoparticles of the invention are typically sufficiently long (at least 2, or at least 4 or at least 6 carbon atoms) and hydrophobic.

Typically, in the context of the present invention, the optionally substituted alkyl-based ligands are selected from the group comprising hexane-, pentane-, octane-, undecane-, hexadecane-based ligands.

Substituted alkyl-based ligands, substituted $C_4$-$C_{30}$ alkyl based ligands, and substituted $C_4$-$C_{30}$ carboxyalkyls of virucidal nanoparticles of the present invention, are substituted with 1, 2, 3, 4 or 5 substituents independently selected from the group comprising alkenyl, alkenylthio, alkenyloxy, alkoxy, alkoxyalkoxy, alkoxyalkoxyalkoxy, alkoxyalkoxyalkyl, alkoxyalkyl, alkoxycarbonyl, alkoxycarbonylalkoxy, alkoxycarbonylalkyl, alkoxysulfonyl, alkyl, alkylamidoalkyl, alkylcarbonyl, alkylcarbonylalkoxy, alkylcarbonylalkyl, alkylcarbonylalkylthio, alkylcarbonyloxy, alkylcarbonylthio, alkylsulfinyl, alkylsulfinylalkyl, alkyl sulfonyl, alkylsulfonylalkyl, alkylthio, alkylthio alkyl, alkylthioalkoxy, alkynyl, alkynyloxy, alkynylthio, aryl, arylcarbonyl, aryloxy, arylsulfonyl, carboxy, carboxyalkoxy, carboxyalkyl, cyano, cyanoalkoxy, cyanoalkyl, cyanoalkylthio, 1,3-dioxolanyl, dioxanyl, dithianyl, ethylenedioxy, formyl, formylalkoxy, formylalkyl, haloalkenyl, halo alkenyloxy, haloalkoxy, haloalkyl, haloalkynyl, halo alkynyloxy, halogen, heterocycle, heterocyclocarbonyl, heterocycloxy, heterocyclosulfonyl, hydroxy, hydroxyalkoxy, hydroxyalkyl, mercapto, mercapto alkoxy, mercapto alkyl, methylenedioxy, and nitro. Preferably substituted alkyl-based ligands, substituted $C_4$-$C_{30}$ alkyl-based ligands, and substituted $C_4$-$C_{30}$ carboxyalkyls are substituted with one mercapto group (replacing the corresponding oxygen of the unmodified cyclodextrin). Preferred substituted alkyl-based ligand is alkylamidoalkyl substituted $C_4$-$C_{30}$ or $C_2$ to $C_{28}$ or $C_4$ to $C_{13}$ alkyl-based ligand.

The percentage ratio between the ligands and the ligands comprising a trisaccharides moiety is of 75%:25% to 95%:5%; preferably 88%:12%.

In the context of the present disclosure, "plurality of ligands" refers to a virucidal nanoparticle core that is coated, partially or completely, by a plurality of ligands of the invention, wherein at least a portion of said ligands comprise a trisaccharides moiety of the invention. The coating can be homogenous, unstructured or structured. In some embodiments, the virucidal nanoparticle comprises very high density (HD) of ligands comprising trisaccharide moiety of the invention, for example 25% of total ligands. In some embodiments, the virucidal nanoparticle comprises about 2 to about 5 ligands of the invention per nm$^2$, wherein at least a portion of said ligands comprise a trisaccharide moiety. In other embodiments, the virucidal nanoparticle comprises four ligands of the invention per $nm^2$, wherein at least a portion of such ligands comprise a trisaccharide moiety.

In some embodiments of the invention, the plurality of ligands of the invention comprises a mixture of at least two structurally different ligands, such as polyethylene glycol 5 (PEG(5)) and 16-mercaptohexadeconic acid (C15). The term "mixture of at least two structurally different ligands", as used herein, refers to a combination of two or more ligands of the invention as defined above, wherein said ligands differ from each other in their chemical composition in at least one position. The mixture can advantageously be organized so that the ligands bearing no trisaccharide moiety provide optimal spacing for the ligands that do bear a trisaccharide moiety and do not hinder the interactions between the trisaccharide moieties and the influenza viral HA. Thus, a percentage ratio will exist between ligands not bearing versus those bearing a trisaccharide moiety, ranging from about 75:25 to about 95:5, preferably about 88:12.

According to an embodiment of the invention, PEG(5) & 16-mercaptohexadeconic acid (C15) mixed ligand gold nanoparticles (NPs) have been synthesized. PEG(5) enhances water solubility of NPs whereas C15 is the ligand to graft the trisaccharide. The ligand choice was based on two reasons: 1) C15 is sufficiently long to target three sialic acid binding points, that are ~4 nm apart, on the HA, 2) Carbon based rigid ligand enhances the virucidal activity.

The ligands are generally present on the surface of the core in an amount that optimizes binding of the trisaccharide moieties to the influenza hemagglutinin. The core has typically four ligands per $nm^2$. In some embodiments, the core has about 2 to about 5 ligands per $nm^2$. Important advantages of the virucidal nanoparticles of the invention is that detailed toxicity analysis did not show any alteration of the tissue structure nor release of pro-inflammatory cytokines. In vivo tests showed that the treatment with the virucidal nanoparticles of the invention significantly improved the health condition of infected mice and reduced the viral load in the lungs, independently of the addition of the drug before or after infection.

Another aspect of the invention discloses a pharmaceutical composition comprising an effective amount of one or more virucidal nanoparticles of the invention and at least one pharmaceutically acceptable excipient, carrier and/or diluent.

As to the appropriate excipients, carriers and diluents, reference may be made to the standard literature describing these, e.g. to chapter 25.2 of Vol. 5 of "Comprehensive Medicinal Chemistry", Pergamon Press 1990, and to "Lexikon der Hilfsstoffe für Pharmazie, Kosmetik und angrenzende Gebiete", by H. P. Fiedler, Editio Cantor, 2002. The term "pharmaceutically acceptable carrier, excipient and/or diluent" means a carrier, excipient or diluent that is useful in preparing a pharmaceutical composition that is generally safe, and possesses acceptable toxicities. Acceptable carriers, excipients or diluents include those that are acceptable for veterinary use as well as human pharmaceutical use. A "pharmaceutically acceptable carrier, excipient and/or diluent" as used in the specification and claims includes both one and more than one such carrier, excipient and/or diluent.

Optionally, the pharmaceutical composition of the present invention further comprises one or more additional active agents, preferably anti-viral agents.

The virucidal nanoparticles of the invention that are used in the methods of the present invention can be incorporated into a variety of formulations and medicaments for therapeutic administration. More particularly, a virucidal nanoparticle as provided herein can be formulated into pharmaceutical compositions by combination with appropriate, pharmaceutically acceptable carriers, excipients and/or diluents, and can be formulated into preparations in solid, semi-solid, liquid or gaseous forms, such as tablets, capsules, pills, powders, granules, dragees, gels, slurries, ointments, solutions, suppositories, injections, inhalants and aerosols. As such, administration of the virucidal nanoparticles can be achieved in various ways, including oral, buccal, inhalation (pulmonary, nasal), rectal, parenteral, intraperitoneal, intradermal, transdermal, intracranial and/or intratracheal administration. Moreover, the virucidal nanoparticles can be administered in a local rather than systemic manner, in a depot or sustained release formulation. The virucidal nanoparticles can be formulated with common excipients, diluents or carriers, and compressed into tablets, or formulated as elixirs or solutions for convenient oral administration, or administered by the intramuscular or intravenous routes. The virucidal nanoparticles can be administered transdermally, and can be formulated as sustained release dosage forms and the like. The virucidal nanoparticles can be administered alone, in combination with each other, or they can be used in combination with other known compounds. Suitable formulations for use in the present invention are found in Remington's Pharmaceutical Sciences (Mack Publishing Company (1985) Philadelphia, PA, 17th ed.), which is incorporated herein by reference. Moreover, for a brief review of methods for drug delivery, see, Langer, Science (1990) 249:1527-1533, which is incorporated herein by reference.

Sustained-release preparations may be prepared. Suitable examples of sustained-release preparations include semi permeable matrices of solid hydrophobic polymers containing the virucidal nanoparticles of the invention, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and [gamma]ethyl-L-glutamate, non-degradable ethylenevinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The virucidal nanoparticles of the present invention may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nanoparticles and nanocapsules) or in macroemulsions. Such techniques are disclosed in Remington's Pharmaceutical Sciences 16th edition, Osol, A. Ed. (1980).

The pharmaceutical compositions described herein can be manufactured in a manner that is known to those of skill in the art, i.e., by means of conventional mixing, dissolving, granulating, dragee-making, levigating, emulsifying, encapsulating, entrapping or lyophilizing processes. The following methods and excipients are merely exemplary and are in no way limiting. For injection, a virucidal nanoparticle (and optionally another active agent) can be formulated into preparations by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Preferably, the virucidal nanoparticles of the present invention can be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

Preferably, pharmaceutical formulations for parenteral administration include aqueous solutions of the virucidal nanoparticles in water-soluble form. Additionally, suspensions of the virucidal nanoparticles can be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances that increase the viscosity of the suspension, such as sodium carboxymethyl cellulose, sorbitol, or dextran. Optionally, the suspension can also contain suitable stabilizers or agents that increase the solubility of the virucidal nanoparticles to allow for the preparation of highly concentrated solutions.

The amount of a virucidal nanoparticle of the invention that can be combined with a carrier material to produce a single dosage form will vary depending upon the viral disease treated, the mammalian species, and the particular mode of administration. It will be also understood, that the specific dose level for any particular patient will depend on a variety of factors including the activity of the specific compound employed; the age, body weight, general health, sex and diet of the individual being treated; the time and route of administration; the rate of excretion; other drugs that have previously been administered; and the severity of the particular viral disease undergoing therapy, as is well understood by those of skill in the area.

Further aspect of the invention provides a method of treating and/or preventing influenza virus infections and/or diseases associated with influenza viruses, comprising administering to a subject in need thereof, a therapeutically effective amount of one or more virucidal nanoparticles of the invention.

Another aspect of the invention provides the virucidal nanoparticles of the invention for use in treating and/or preventing influenza virus infections and/or diseases associated with influenza viruses.

As used herein the terms "subject" or "patient" are well-recognized in the art, and, are used interchangeably herein to refer to a mammal, including dog, cat, rat, mouse, monkey, cow, horse, goat, sheep, pig, camel, and, most preferably, a human. Other animals, such as a chicken, are also encompassed by these terms. In preferred embodiments, the terms "subject" or "patient" refer to a human and animals, such as dog, cat, rat, mouse, monkey, cow, horse, goat, sheep, pig, camel, chicken. In some embodiments, the subject is a subject in need of treatment or a subject being infected by an influenza virus. In other embodiment, a subject can be an animal infected by avian influenza, such as a chicken. However, in other embodiments, the subject can be a healthy subject or a subject who has already undergone treatment. The term does not denote a particular age or sex. Thus, adult, children and newborn subjects, whether male or female, are intended to be covered.

"Treatment" refers to both therapeutic treatment and prophylactic or preventative measures. Those in need of treatment include those already being infected by an influenza virus, as well as those in which the influenza viral infection is to be prevented. Hence, the mammal, preferably human, to be treated herein may have been diagnosed as being infected by an influenza virus, or may be predisposed or susceptible to be infected by an influenza virus. Treatment includes ameliorating at least one symptom of, curing and/or preventing the development of a disease or condition due to influenza viral infection. Preventing is meant attenuating or reducing the ability of an influenza virus to cause infection or disease, for example by affecting a post-entry viral event.

"Mammal" for purposes of treatment refers to any animal classified as a mammal, including humans, domestic and farm animals or pet animals, such as dogs, horses, cats, cows, monkeys etc. Preferably, the mammal is human.

The term "therapeutically effective amount" refers to an amount of a virucidal nanoparticle of the invention effective to alter an influenza virus, and to render it inert, in a recipient subject, and/or if its presence results in a detectable change in the physiology of a recipient subject, for example ameliorates at least one symptom associated with a viral infection, prevents or reduces the rate transmission of at least one viral agent.

Another aspect of the invention provides a virucidal composition comprising an effective amount of one or more virucidal nanoparticles of the invention and optionally at least one suitable carrier or aerosol carrier. "An effective amount" refers to the amount sufficient for irreversibly inhibiting influenza viruses; i.e. sufficient for obtaining virucidal effect. In an embodiment, the suitable carrier is selected from the group comprising stabilisers, fragrance, colorants, emulsifiers, thickeners, wetting agents, or mixtures thereof. In another embodiment, the virucidal composition can be in the form of a liquid, a gel, a foam, a spray or an emulsion. In a further embodiment, the virucidal composition can be an air freshener, a sterilizing solution or a disinfecting solution.

Another aspect of the invention provides a device (or a product) comprising the virucidal composition of the invention or one or more virucidal nanoparticles of the invention and means for applying and/or dispensing the virucidal nanoparticles of the invention. In another embodiment, the means comprise a dispenser, a spray applicator or a solid support soaked with the virucidal nanoparticles of the invention. In another embodiment, the support is a woven or non-woven fabric, a textile, a paper towel, cotton wool, an absorbent polymer sheet, or a sponge.

Another aspect of the invention provides a method of disinfection and/or sterilization using the virucidal nanoparticles of the invention or the virucidal composition of the invention or the pharmaceutical composition of the invention.

In a preferred embodiment, the method of disinfection and/or sterilization comprises the steps of (i) providing at least one virucidal nanoparticle of the invention or a virucidal composition of the invention, or pharmaceutical composition of the invention, (ii) contacting an influenza virus-contaminated surface or a surface suspected to be contaminated by influenza virus with the at least one virucidal nanoparticle of the invention or a virucidal composition of the invention or pharmaceutical composition of the invention for a time sufficient to obtain virucidal effect. In some embodiments, the influenza virus-contaminated surface is human or animal skin. In other embodiments, the influenza virus-contaminated surface is a non-living surface, such as medical equipments, clothing, masks, furnitures, rooms, etc.

Another aspect of the invention provides a use of a virucidal nanoparticle of the invention or a virucidal composition of the invention or a pharmaceutical composition of the invention for sterilization and/or for disinfection. In some embodiments, sterilization and disinfection is for influenza virus-contaminated surfaces or surfaces suspected to be contaminated by influenza viruses. In some preferred embodiments, the surfaces are human or animal skin. In other preferred embodiments, the surfaces are non-living surfaces, such as medical equipments, clothing, masks, furnitures, rooms, etc. In an embodiment, the virucidal composition of the invention or the pharmaceutical composition of the invention is used as virucidal hand disinfectant for frequent use. In another embodiment, the virucidal composition of the invention or the pharmaceutical composition of the invention is applied by spraying. In a further embodiment, the virucidal composition of the invention of the pharmaceutical composition of the invention is applied on a protective mask.

Those skilled in the art will appreciate that the invention described herein is susceptible to variations and modifications other than those specifically described. It is to be understood that the invention includes all such variations and modifications without departing from the spirit or essential characteristics thereof. The invention also includes all of the steps, features, compositions and compounds referred to or indicated in this specification, individually or collectively, and any and all combinations or any two or more of said steps or features. The present disclosure is therefore to be considered as in all aspects illustrated and not restrictive, the scope of the invention being indicated by the appended Claims, and all changes which come within the meaning and range of equivalency are intended to be embraced therein.

The foregoing description will be more fully understood with reference to the following Examples. Such Examples, are, however, exemplary of methods of practising the present invention and are not intended to limit the scope of the invention.

EXAMPLES

Experimental Data

Density Assay

NPs at three different 6-sialyl-N-acetyllactoseamine (6'SLN) densities were synthetized in order to demonstrate the optimum 6'SLN density (FIG. 1). Control experiments with PEG(5) and 3-sialyl-N-acetyllactoseamine (3'SLN)—coated gold NPs were conducted as well.

Comparative dose-response studies were conducted on two influenza A strains H1N1 (Neth/09) and H3N2 (Sing/04) and one B strain, Yamagata. LD-6'SLN NPs have the lowest half inhibitory concentration ($EC_{50}$) against all the viruses tested. NPs, in general, inhibited influenza A subtype better than B subtype.

TABLE 1

In vitro half inhibitory ($EC_{50}$) and cytotoxic concentrations ($CC_{50}$) of different NPs against H1N1 Neth/09 strain. The molarities were calculated based on NPs and trisaccharides/NP separately.

| | Influenza Strain | $EC_{50}$ (µg/mL) | $EC_{50}$ NPs (nM) | $EC_{50}$ 6'SLN (nM) | $CC_{50}$ (µg/ml) |
|---|---|---|---|---|---|
| LD 6'SLN NPs (18 6' SLN/NP) | H1N1 Neth/09 | 0.13 | 0.64 | 11.5 | >500 |
| HD 6'SLN NPs (38 6'SLN/NP) | H1N1 Neth/09 | 0.45 | 2.2 | 83 | >500 |
| LD(-) 6'SLN NPs (8 6'SLN/NP) | H1N1 Neth/09 | 1.1 | 5.4 | 43 | >500 |
| LD 3'SLN NPs (18 3'SLN/NP) | H1N1 Neth/09 | 5.3 | 27.2 | 489 | >500 |
| PEG5 NPs | H1N1Neth/09 | N/A | N/A | N/A | >500 |

TABLE 2

$EC_{50}$ and $CC_{50}$ of different NPs against H3N2 Sing/04 strain.

| | Influenza Strain | $EC_{50}$ (µg/mL) | $EC_{50}$ NPs (nM) | $EC_{50}$ 6'SLN (nM) | $CC_{50}$ (µg/ml) |
|---|---|---|---|---|---|
| LD 6'SLN NPs (18 6'SLN/NP) | H3N2 SING/04 | 0.58 | 2.8 | 50.4 | >500 |
| HD 6'SLN NPs (38 6'SLN/NP) | H3N2 SING/04 | 1.12 | 5.9 | 224.4 | >500 |
| LD(-) 6'SLN NPs (8 6'SLN/NP) | H3N2 SING/04 | 1.9 | 9.4 | 75.2 | >500 |
| LD 3'SLN NPs (18 3'SLN/NP) | H3N2 SING/04 | 4.5 | 22 | 396 | >500 |
| PEG5 NPs | H3N2 SING/04 | N/A | N/A | N/A | >500 |

TABLE 3

$EC_{50}$ and $CC_{50}$ of different NPs against Influenza B/Yamagata.

| | Influenza Strain | $EC_{50}$ (µg/mL) | $EC_{50}$ NPs (nM) | $EC_{50}$ 6'SLN (nM) | $CC_{50}$ (µg/ml) |
|---|---|---|---|---|---|
| LD 6'SLN NPs (18 6'SLN/NP) | B/Yamagata | 13.7 | 67 | 1206 | >500 |
| HD 6'SLN NPs (38 6'SLN/NP) | B/Yamagata | 17.25 | 85 | 3230 | >500 |
| LD(-) 6'SLN NPs (8 6'SLN/NP) | B/Yamagata | 53.3 | 260 | 2080 | >500 |
| LD 3'SLN NPs (18 3'SLN/NP) | B/Yamagata | >100 | >100 | >1000 | >500 |
| PEG5 NPs | B/Yamagata | N/A | N/A | N/A | >500 |

Virucidal assays were then conducted, to determine whether the mechanism of inhibition is irreversible. In a virucidal assay, the NPs were incubated with the virus at corresponding $IC_{99}$ concentration for a certain amount of time. Serial dilutions were then conducted of the inoculum and the residual infectivity of the virus was measured. Virucidal activity of LD 6'SLN NPs against Neth/09 and Sing/04 strains was tested by increasing the virus concentration ten times relative to the dose-response experiments. The titer of Neth/09 strain was reduced by 2 logs whereas Sing/04 was reduced by 1.5 logs. 1-2 logs reduction in virus titer indicates that the virus is irreversibly inhibited.

TEM Studies to Demonstrate Virus-NP Interaction

Figure 2:
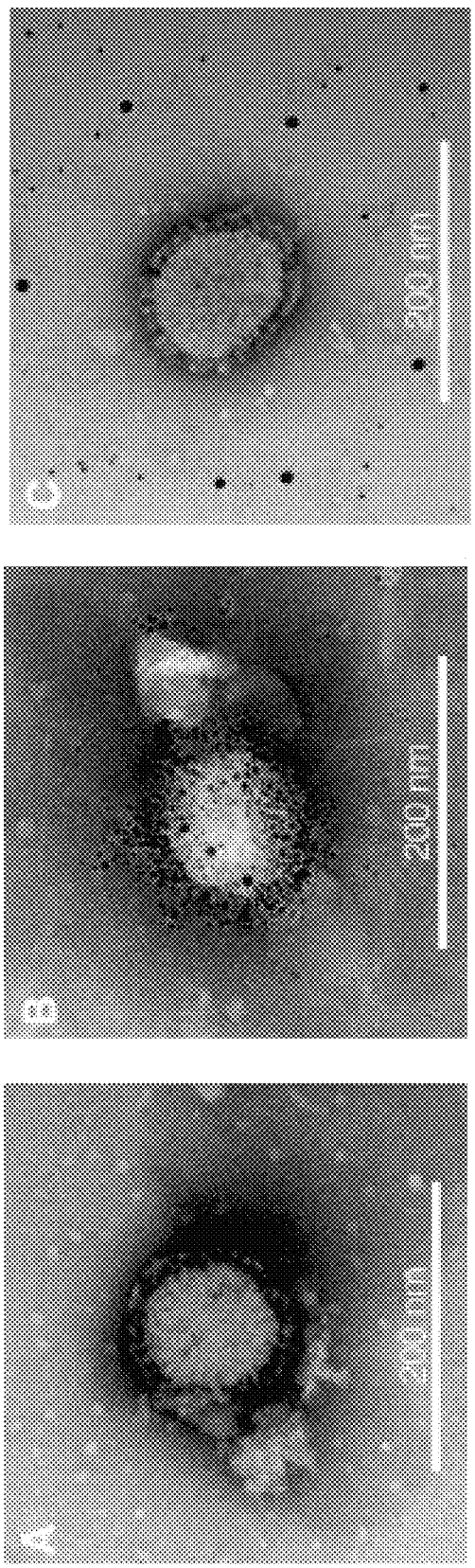
FIG. 2 shows TEM images of H3N2 virus Vic/11 strain: without NPs (A), the virus after 1 hour incubation with LD 6'SLN NPs (B) and with PEG(5) NPs (C).

The virus-NP interaction were demonstrated also with electron microscopy (TEM). H3N2 Vic/11 virus was incubated with LD 6'SLN NPs for 1 hour. After preparation of TEM grids, methyl tungsten staining was conducted. Majority of viruses were fully covered with LD 6'SLN NPs (FIG. 2B). The control experiments were conducted with PEG(5) NPs in which the NPs were all around but not attached to the viral envelop (FIG. 2C).

Potential of the NPs to Inhibit Avian Influenza Virus

Influenza pandemics usually appear when animal influenza strains mix with human influenza strains. Therefore, the next goal is to irreversibly inhibit the avian flu strains with NPs of the invention. Preliminary research was conducted with an egg-adapted virus strain, CAL/09. Neth/09 and CAL/09 are two very similar human H1N1 strains. LD-6'SLN NPs have a strong activity on the Neth/09 strain. However, CAL/09 strain, which is replicated using chicken eggs, binds LD 3'SLN NPs with higher affinity (Table 4). This result indicate that LD-3'SLN NPs inhibit avian influenza strains.

TABLE 4

Egg adapted virus strain prefers −2,3 linkage, whereas mouse adapted strain prefers −2,6 linkage.

|  | Neth/09 Mouse Adapted $EC_{50}$ (µg/mL) | CAL/09 Egg Adapted $EC_{50}$ (µg/mL) |
|---|---|---|
| LD-6'SLN | 0.13 | 34.9 |
| LD-3'SLN | 5.13 | 1.18 |

From Gold Core to Cyclodextrin Core

Human influenza virus was irreversibly inhibited with C15-6'SLN grafted gold NPs. However, it is important to change the gold core to an organic material for pharmaceutical applications. Among different organic materials such as polymers, dendrimers and dendrons, cyclodextrin (CD) is the preferred core to graft ligands bearing 6'SLN in order to target HA.

Figure 3:
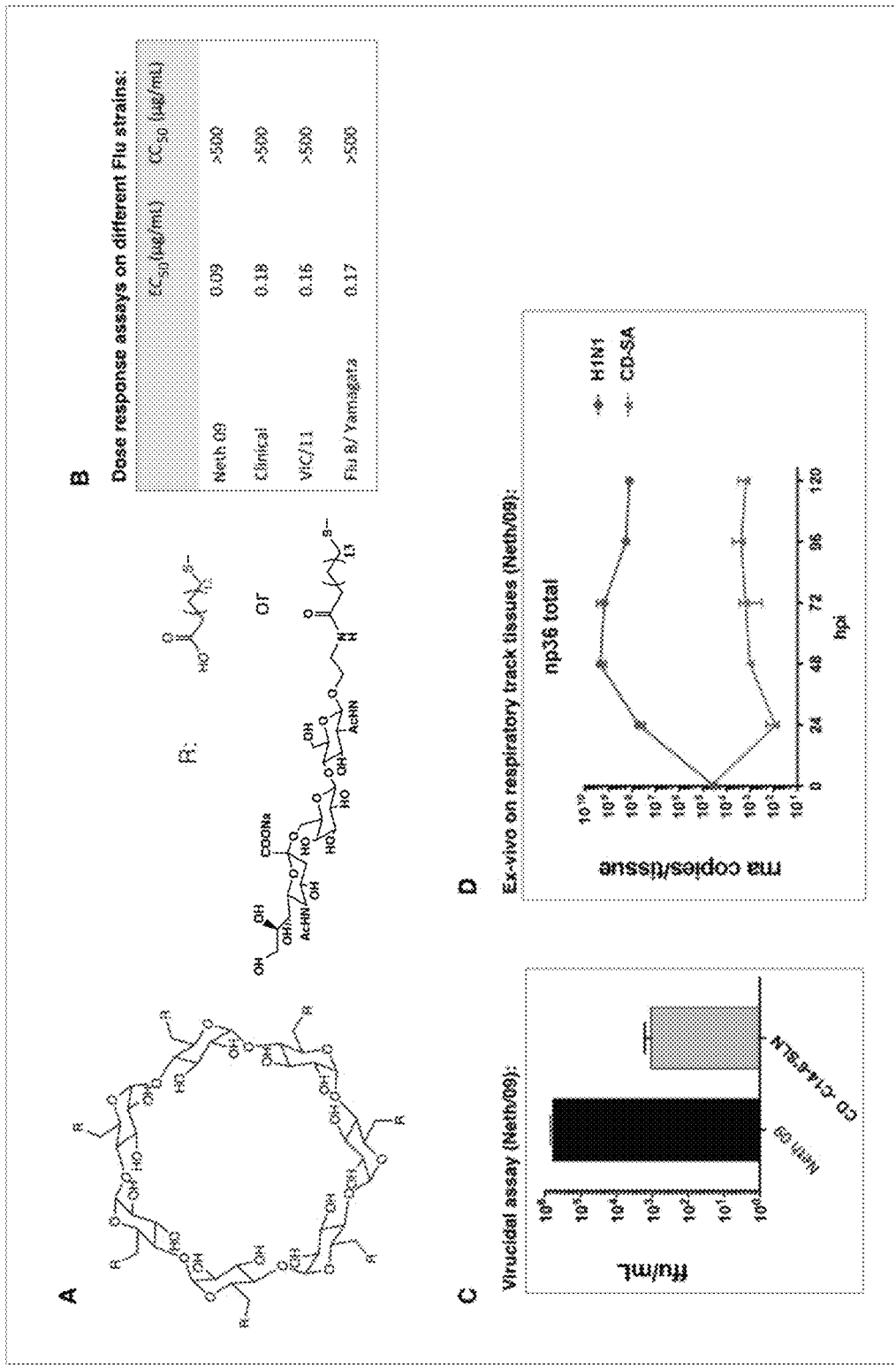
FIG. 3 shows chemical structure of C15-6'SLN modified β-CD (A). EC$_{50}$ concentrations of the modified CD against different influenza strains (B). Virucidal activity against Neth/09 strain (C) ex vivo experiment on the MucilAir (D). Illustration of modified CD interacting with HA globular head (E).

The size of CD (d~1.5 nm) is comparable to gold (metal) NPs of the invention (~3 nm) and matches well with the HA globular head (~5 nm). Similar to gold (metal) NPs, cyclodextrin has a rigid chemical structure, which contributes to the virucidal activity together with the ligand. Also, beta-cyclodextrin can have maximum of 7 trisaccharides (and more preferably 3 or 4 trisaccharides), three being the exact number of sialic acid binding points in the HA globular head (FIG. 3A). Therefore, β-CD was modified with C15-6'SLN in a very similar way to gold nanoparticles.

In comparison to previous organic materials bearing sialic acid, significantly lower $EC_{50}$ values were obtained on different human influenza viruses (FIG. 3B). The virucidal activity of modified cyclodextrin was proven with both in vivo and ex vivo experiments in which the viral titer was reduced by several logs (FIGS. 3C and D). The successful results in ex vivo indicate that modified cyclodextrin will irreversibly inhibit the virus in vivo.

It is herein shown that the choice of trisaccharide as well as the ligand is very important to irreversibly inhibit the human influenza viruses with nano-materials. C15-6'SLN ligand on two different cores, gold nanoparticles and cyclodextrin, inhibited several strains of human influenza virus at very low nano-material concentrations. $EC_{50}$ concentrations in the low nM range (1-100 nM) were achieved, relative to trisaccharide units, whereas literature $EC_{50}$ values were 50 to 500 times higher for similar materials.

Figure 5:
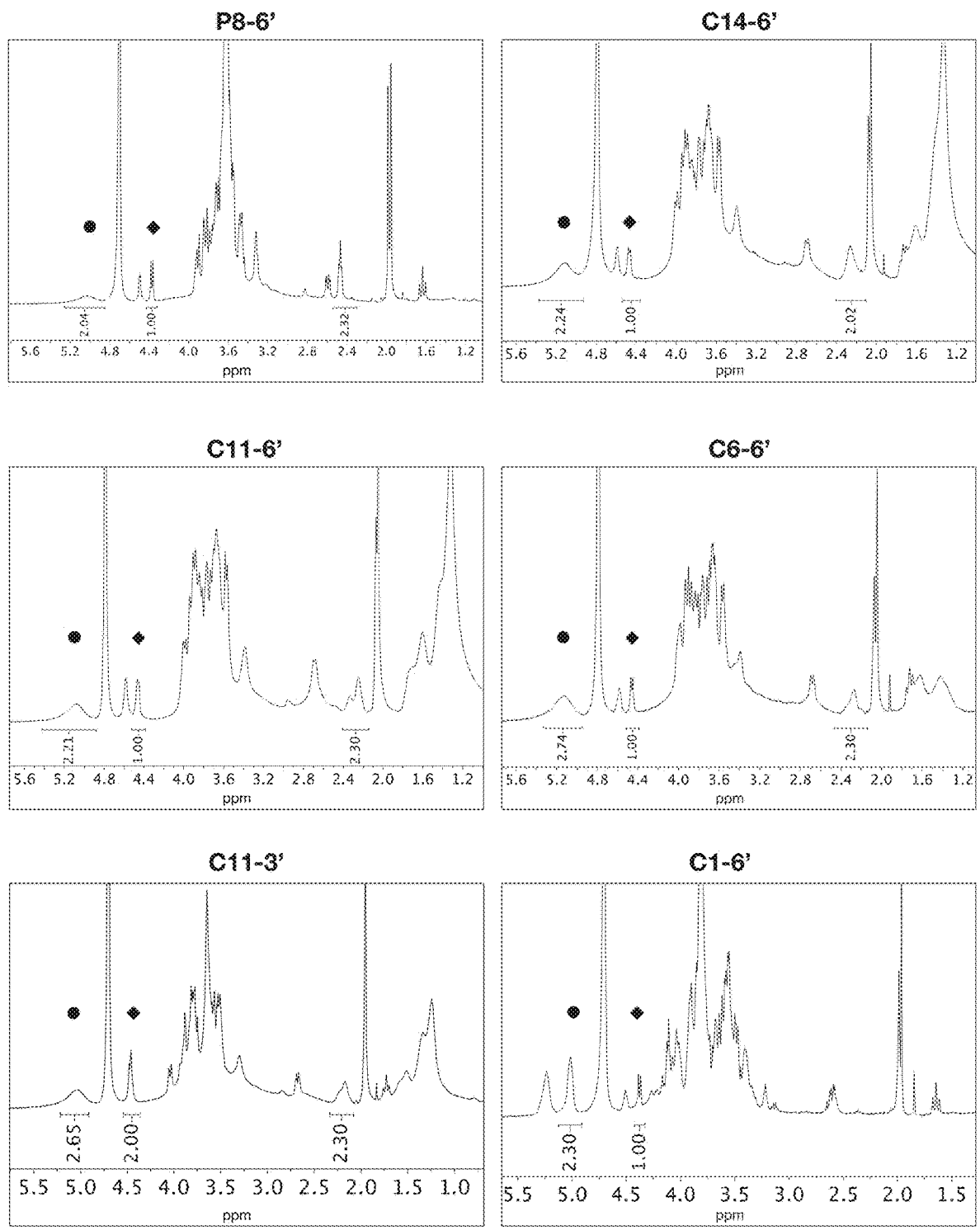
FIG. 5 shows $^1$H NMR studies were conducted in order to characterize the modified cyclodextrins shown in FIG. 4. Average number of 6'SLN or 3'SLN per ß-cyclodextrin was calculated by comparing a distinctive peak from the trisaccharide (♦) to the one from ß-cyclodextrin (●). Both peaks correspond to a single hydrogen.
Figure 6:
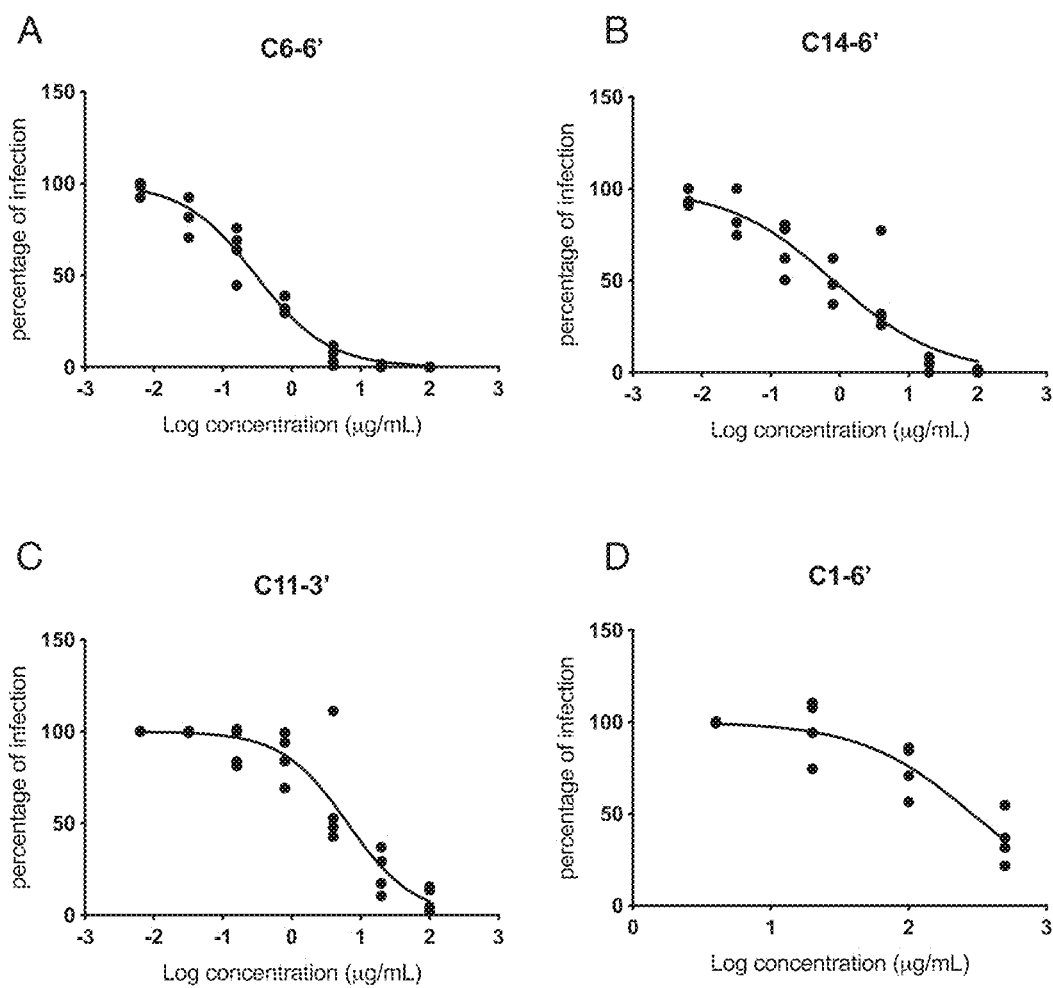
FIG. 6 shows dose-response curves demonstrating the antiviral activity of C6-6' (A), C14-6' (B), C11-3' (C) and C1-6' (D) against A/Netherlands/2009 H1N1. The results are the mean of 2 independent experiments performed in duplicates.

In Vitro Antiviral Activity of Modified Cyclodextrins

β-cyclodextrin (β-CD) was modified with different ligands, with and without trisaccharides, in order to investigate the relationship between the chemical structure and the antiviral activity. Exemplary modified cyclodextrins are shown in FIG. 4. They bear a comparable number of trisaccharides (see FIG. 5 and Table 5), determined with $^1$H Nuclear Magnetic Resonance Spectroscopy (NMR)). Dose-response assays against influenza A/Netherlands/2009 (H1N1) strain (A/NL/09), were conducted to compare the inhibitory activity of these NPs (FIG. 6). The infection was quantified with immunocytochemical assays, 24 hours post-infection (hpi). β-CDs bearing a sufficiently long, hydrophobic ligand and 6'SLN end-group (C6-6'SLN, C11-6'SLN, and C14-6'SLN) showed strong inhibitory activity against infection of cells by the influenza A/NL/09, having $EC_{50}$ values in the nanomolar range. On the other hand, the β-CD with a shorter ligand, C1-6'SLN, poorly inhibited the infection. Introducing a sufficiently long ligand clearly enhanced the end-group flexibility; hence the inhibitory concentrations decreased. The $EC_{50}$ was comparable (yet slightly higher) when the hydrophobic ligand was replaced with a hydrophilic PEG8 ligand (PEG8-6'SLN).

TABLE 5

Average number of 6'SLN or 3'SLN per ß-cyclodextrin determined by $^1$H NMR and corresponding molecular weights.

|  | Number of spacers/CD | Number of 6'SLN/CD | Molecular weight (kDa) |
|---|---|---|---|
| P8-6' | 4 | 3.5 | 5.7 |
| C14-6' | 3.1 | 3 | 4.1 |
| C11-6' | 3.6 | 3.1 | 4.1 |
| C6-6' | 2.8 | 2.7 | 3.4 |
| C11-3' | 3 | 2.7 | 3.9 |
| C1-6' | — | 3 | 3.5 |

Figure 7:
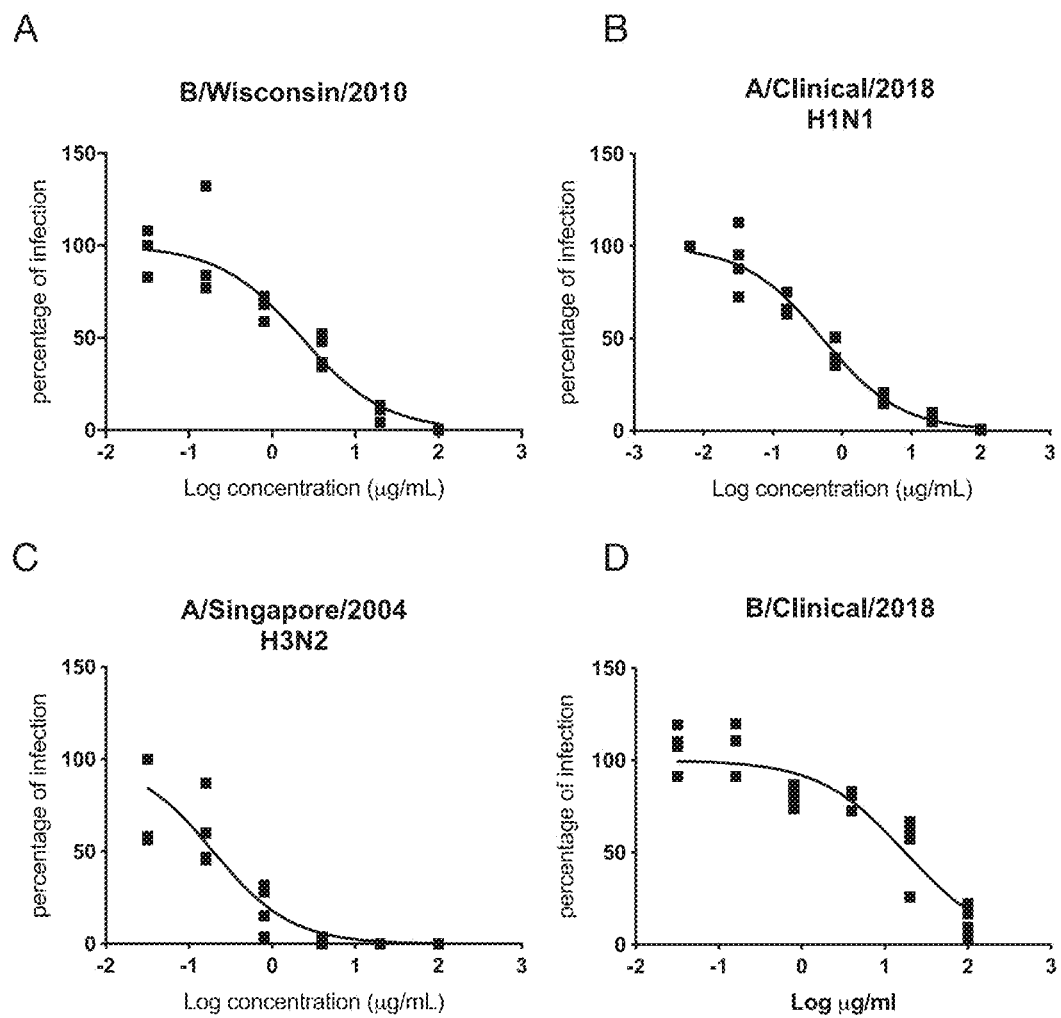
FIG. 7 shows dose-response curves demonstrating the antiviral activity of C11-6' against B/Wisconsin/2010 (A), A/Clinical/2018 H1N1 (B), A/Singapore/2004 H3N2 (C) and B/Clinical/2018 (D). The results are the mean of 2 independent experiments performed in duplicates.

C11-6'SLN, the nanoparticle that showed the best inhibitory activity against A/NL/09, displayed strong antiviral activity against human influenza strains from both the A and the B types (Table 6 and FIG. 7). Importantly, it inhibited very recent A (H1N1) and B clinical strains (from the 2017/2018 influenza season), isolated from patients in the University Hospital of Geneva and passaged only once in cells. C11-6'SLN did not show any antiviral activity against HSV-2, an HSPG-binding virus, indicating specificity of the compound for sialic acid dependent viruses.

Figure 8:
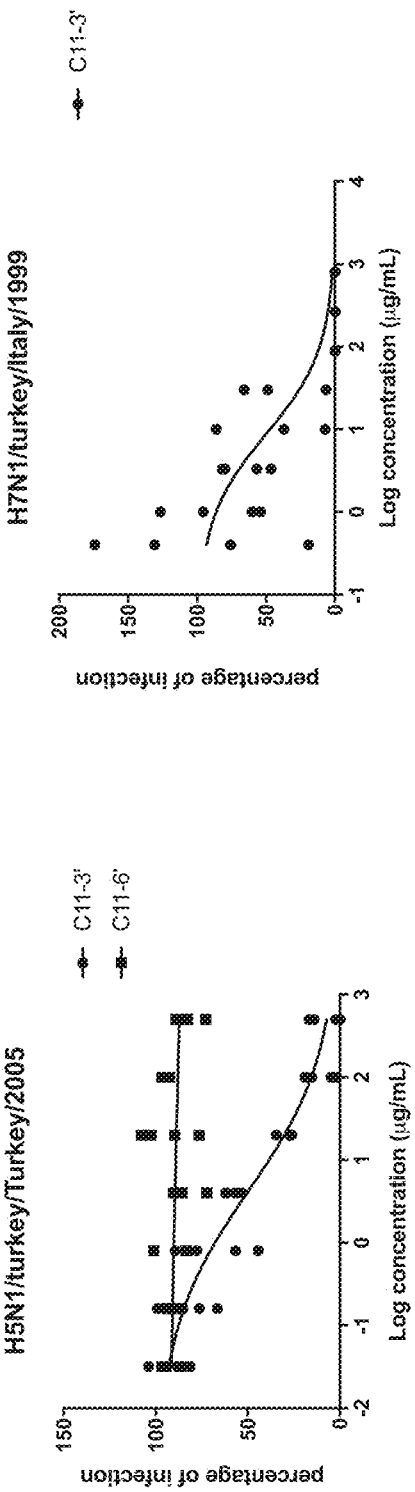
FIG. 8 shows dose-response curves demonstrating the antiviral activity of C11-3' against avian strains A/turkey/Turkey/2005 H5N1 (together with C11-6' control) (A) and A/Turkey/Italy/977/1999 H7N1 (B). In the case of graph A, The infection was quantified with both FACS and ICC methods. The results are the mean of 2 independent experiments performed in duplicates.

6'SLN is known to be specific to human influenza strains whereas 3'SLN is preferred for avian influenza strains as a primary attachment point. To prove the generality of this approach, especially against influenza strains that are known to have the ability of crossing the species barrier, C11-3'SLN was synthesized and tested (FIG. 4) against avian influenza strains. C11-3'SLN successfully inhibited two avian strains, H5N1 and H7N1, at 4.1 and 8.8 µg/ml concentrations respectively (see Table 6). De facto, these results confirm the strategy adopted against human strains. Importantly, one of these avian strains, H5N1, has a significant potential to cause the next influenza pandemic. It was additionally tested whether C11-3'SLN can inhibit a human strain, A/NL/09 and whether C11-6'SLN would also be active against an avian strain, H5N1. C11-3'SLN displayed a good inhibitory activity against A/NL/09 (FIG. 4 and Table 6) whereas C11-6'SLN did not show any activity against H5N1 (Table 6 and FIG. 8). These results are in line with previous literature comparing the binding affinities of avian and human strains to the different types of sialic acids. Avian influenza strains (particularly H5N1 strains) preferentially bind to alpha-2,3 linked sialic acid, which has a thin and straight trans conformation. On the other hand, the wider sialic acid binding site of human strains can accommodate both the bulky cis conformation of alpha-2,6 linked sialic acid and narrower-2,3 linked sialic acid.

TABLE 6

Inhibitory activity of C11-6'SLN and C11-3'SLN against different influenza strains.

| | Compound | $CC_{50}$ (μg/mL) | $EC_{50}$ (ug/mL) | $EC_{50}$† (nM) |
|---|---|---|---|---|
| A/Netherlands/2009 (H1N1) | C11-6' | >100 | 0.18 (0.14-0.24) | 42 |
| | C11-3' | >100 | 6.5 (4.1-10.1) | >1000 |
| A/Clinical/2018 (H1N1) | C11-6' | >100 | 0.5 (0.4-0.67) | 125 |
| Singapore/2004 (H3N2) | C11-6' | >100 | 0.23 (0.16-0.34) | 56.5 |
| B/Wisconsin/2010* | C11-6' | >100 | 2.2 (1.49-3.42) | 500 |
| B/Clinical/2018 | C11-6' | >100 | 20 (10.5-28.7) | >1000 |
| A/turkey/Turkey/2005 (H5N1) | C11-3' | >100 | 4.1 (2.55-6.7) | 931 |
| | C11-6' | >100 | N/A | N/A |
| A/turkey/Italy/1999 (H7N1) | C11-3' | >100 | 8.8 (3.2-26) | >1000 |
| HSV-2 (Control) | C11-6' | >100 | N/A | N/A |

*B Yamagata subtype
†Molar concentrations were determined based on the number of cyclodextrin cores.
$CC_{50}$: Half maximal cytotoxic concentration.

Figure 9:
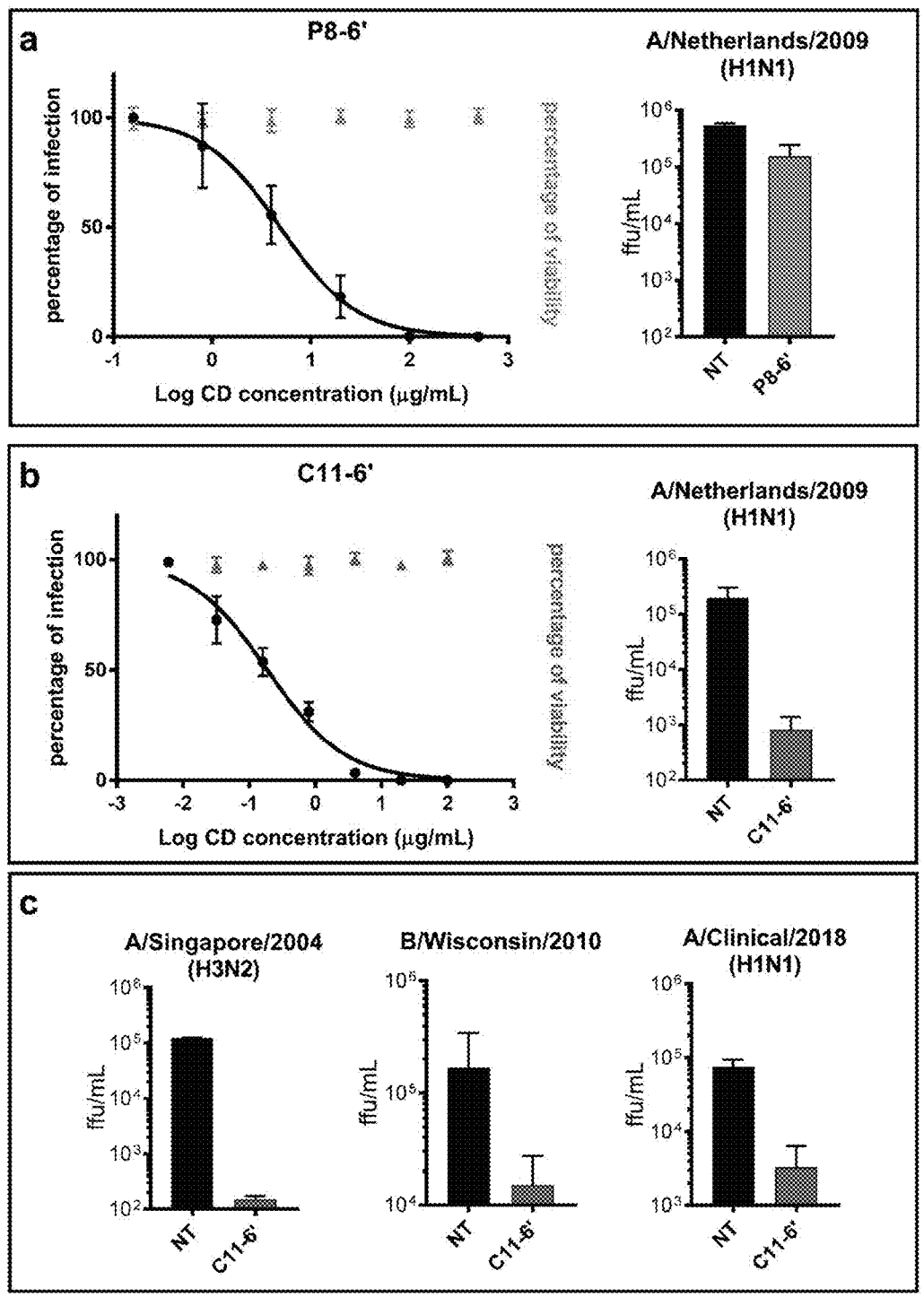
FIG. 9 shows antiviral activity comparison of C11-6' and P8-6' in vitro. Panels (a) and (b) show on the left graphs the inhibitory activity of each compound against A/NL/09, superimposed with the results of the cell viability assays. All the compounds show very similar behaviour. On the right graphs in these panels are shown the results of virucidal (i.e. dilution) test. Note that in the figure's axes ffu stands for focus forming units and NT for non-treated. In (c) C11-6' was tested against the following viral strains: A/Singapore/2004 (H3N2), B/Wisconsin/2010, and A/Clinical/2018 (H1N1). Results are the mean and SEM of 2 independent experiments performed in duplicate.
Figure 10:
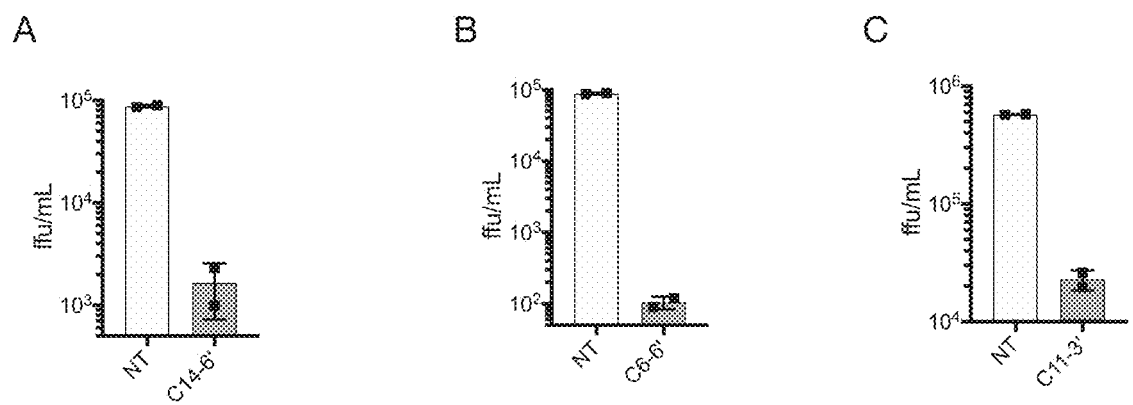
FIG. 10 shows virucidal activity of the C14-6' (A), C6-6' (B) and C11-3' (C) against A/Netherhands/2009 (H1N1). The experiments were performed with a compound concentration of 100 μg/mL. The results are the mean and SEM of 2 independent experiments.

Next, virucidal assays were conducted to determine the mechanism of inhibition, i.e., virucidal (irreversible) or virustatic (reversible). The synthesis of similar nanoparticles sharing the β-cyclodextrin core and the 6'SLN moiety but different ligands highlights a structural feature conferring virucidal action (FIGS. 9 and 10). It was hypothesized that one of the key components of irreversible viral inhibition is that the binding moiety (here 6'SLN) is borne by a hydrophobic ligand. To test this hypothesis, C11-6'SLN and P8-6'SLN were compared. Briefly, amounts of the compounds that provide complete protection (10 μg of C11-6' and 50 μg of P8-6') were incubated with A/NL/09 for 1 h. Serial dilutions of the inocula were conducted followed by evaluation of the infectivity. In the case of C11-6' the graph in (a) shows that complete protection was kept upon dilution and the graphs in (c) show that this property was found against a number of different strains. This is called irreversible (i.e. resistant to dilution) inhibitory activity a virucidal mechanism. In the case of P8-6', the graph in (b) show that while at the initial concentration complete protection was present, upon dilution the difference with the infectivity of the control sample (virus alone) was lost, i.e. the inhibitory effect was found to be reversible (virustatic). These two nanoparticles differ solely in the hydrophobicity of the ligand and show comparable inhibitory activity. In the virucidal assays, C11-6'SLN reduced the virus titer by 1000 times (FIG. 9b), whereas the infection was fully recovered in the case of P8-6'SLN (FIG. 9a). Hence C11-6'SLN has an irreversible inhibitory effect on the virus while the effect of P8-6'SLN is reversible. It is worth mentioning that both nanoparticles are non-toxic to cells (FIGS. 9a and 9b). Virucidal activity of C11-6'SLN against other influenza strains was further investigated confirming its irreversible activity independently of the strain (FIG. 9c).

Ex Vivo Activity of Modified Cyclodextrins

Ex vivo experiments were performed in MucilAir®, a 3D model of human airway reconstituted epithelia. These air-liquid interface cultures perfectly mimic both the pseudostratified architecture (basal, ciliated and goblet cells) and the barrier defence mechanism (i.e. the mucociliary clearance and epithelial cell immunity) of the human upper respiratory epithelium, the main site of Influenza virus replication in humans. Ex vivo experiments were conducted with clinical H1N1 pandemic 09 strain that had not been passaged in cells to exclude any adaptation bias. C11-6'SLN or P8-6'SLN (50 μg/tissue) and the virus ($10^4$ RNA copies/tissue) were first added simultaneously on the apical surface of the tissues, without prior incubation. After four hours, the inocula were removed, the tissues were washed and the progress of the infection was monitored on a daily basis with qPCR from the apical washes of the tissue, without any re-addition of the nanoparticles. C11-6'SLN completely prevented virus replication throughout the entire course of the experiment, while P8-6'SLN slightly reduced viral replication the first two days post-infection (dpi) but not thereafter (FIG. 11a).

Figure 11:
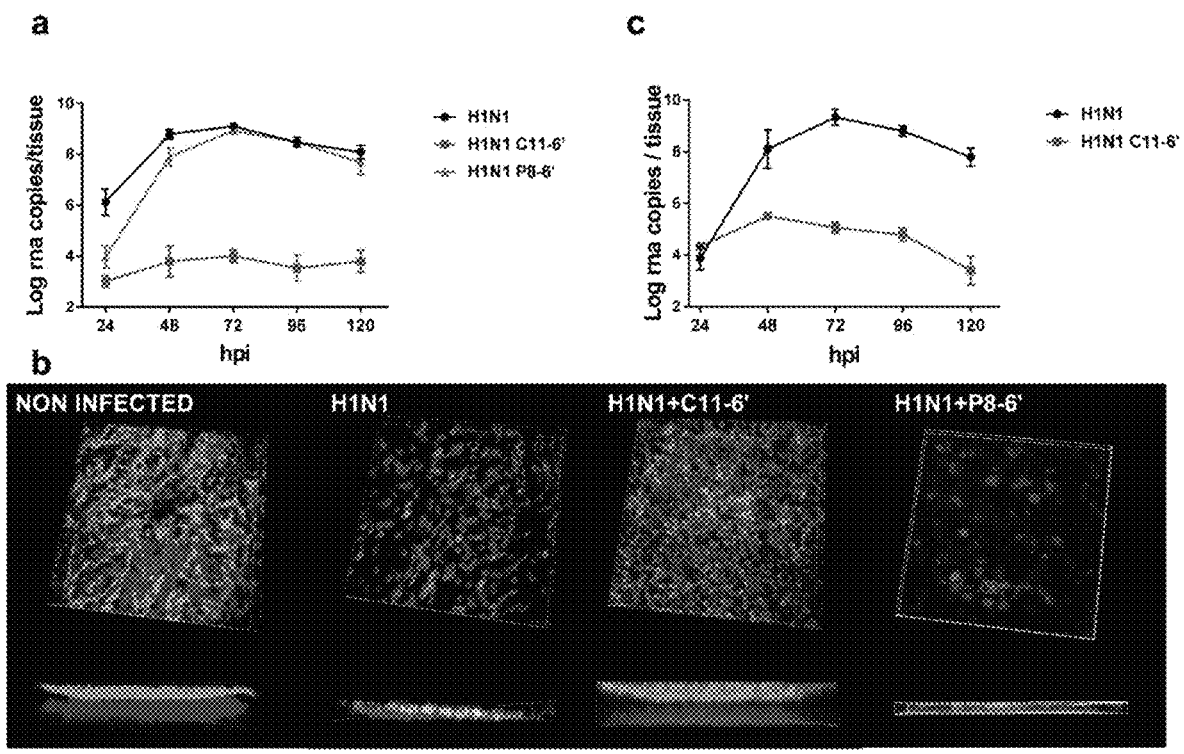
FIG. 11 shows ex vivo inhibitory activity comparison of C11-6' and P8-6'. C11-6' provided a full protection against clinical pandemic H1N1 09 strain in co-treatment condition, whereas P8-6' only provided a minor protection in the beginning of the infection (a).
Figure 12:
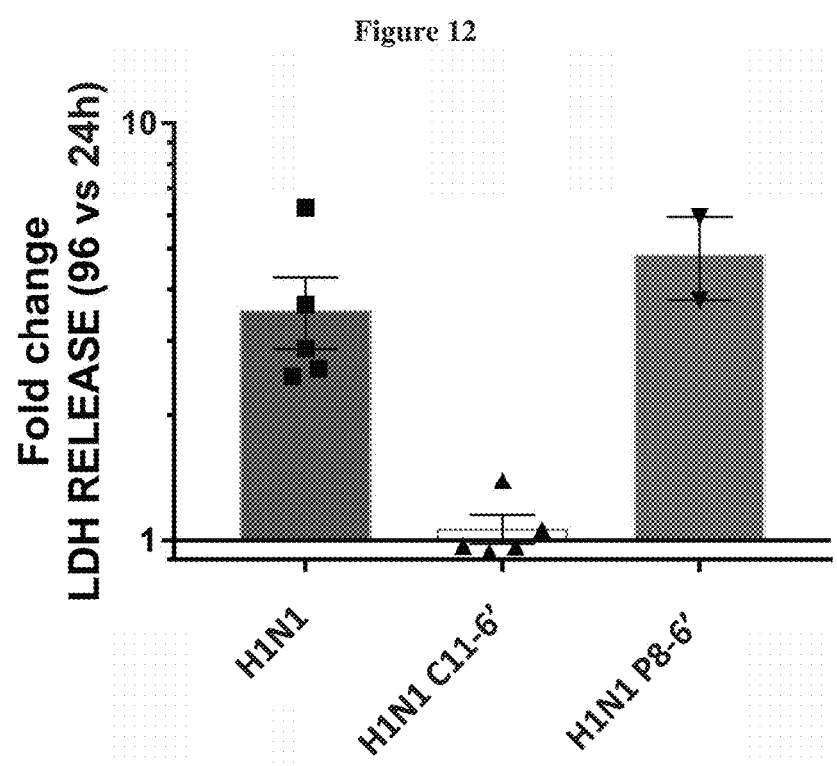
FIG. 12 shows LDH release from infected tissues. Tissues were infected and treated with C11-6' (50 µg) or P8-6' at the time of infection. Apical washes performed at 96 and 24 hpi were subjected to LDH measurement. Results are the mean and SEM of 2 independent experiments for H1N1 and H1N1 C11-6' and of a single experiment performed in duplicate for P8-6'.
Figure 13:
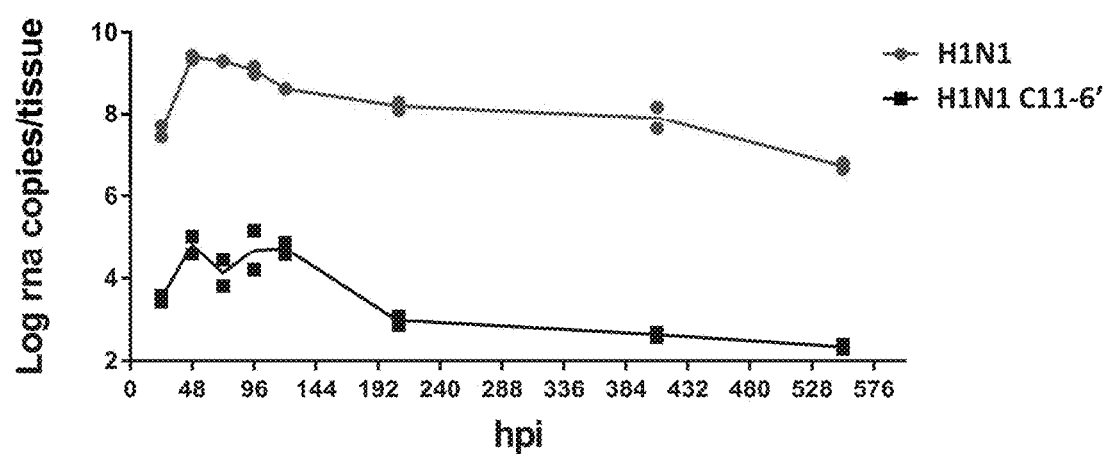
FIG. 13 shows long co-treatment experiment. Tissues were infected and treated with C11-6' (50 µg) at the time of infection. Daily apical washes were collected for the first 5 days, and subsequently at 9, 17 and 23 days, with a wash the previous day in order to evaluate daily virus production. Results are the mean of a single experiment performed in duplicate.
Figure 14:
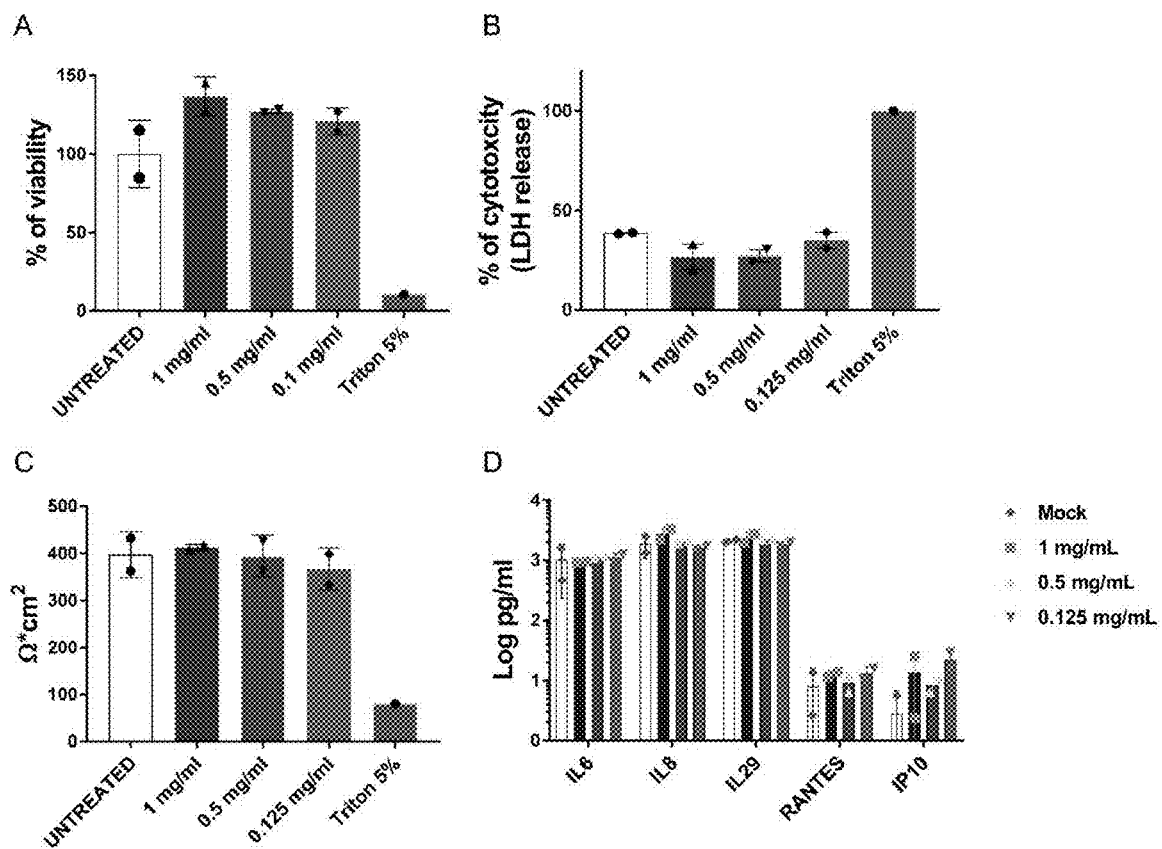
FIG. 14 shows ex vivo toxicity. Tissues were treated with different doses of C11-6' or an equal volume of medium or triton 5% with daily addition. At 96 hours post treatment tissues were subjected to: A) MTT assay, B) LDH assay in which the viability of the tissues was evaluated, C) trans epithelial resistance evaluation and D) ELISAs assay to evaluate the release of pro-inflammatory cytokines. LDH and ELISA were performed on collected basal medium. The experiments are the mean and SEM of 2 independent experiments.

Moreover, in the tissues treated with C11-6'SLN, the inhibition of viral replication was also reflected by the absence of infected cells and the undisturbed morphology of the treated tissues, strikingly different from the untreated or P8-6'SLN-treated tissues (FIG. 11b). Immunofluorescence images and the lack of lactate dehydrogenase (LDH) release in the apical washes demonstrated that the ciliated cell layer as well as the physiological cilia beating and tissue integrity were preserved (FIGS. 11b and 12). In stark contrast, the untreated tissue or the P8-6'SLN-treated controls, presented reduced thickness due to alteration of the ciliated cell layer, and presence of infected cells (FIG. 11b). To exclude that the residual viral level detected by qPCR in the treated tissues was infectious, the tissues were kept in culture for 23 days but no increase in viral titer over time was observed, while the untreated tissues were persistently shedding virus (FIG. 13). Importantly, ex vivo experiments were conducted also in more stringent post-treatment conditions in which C11-6'SLN (30 μg/tissue) was administrated every 24 h for 4 days, starting at 1 dpi to mimic a therapeutic administration. Also, in these conditions, the nanoparticle showed a remarkable inhibitory activity, proving its potential as a therapeutic agent (FIG. 11c). In the same ex vivo model the biocompatibility of high doses of C11-6'SLN, administered daily, was evaluated. C11-6'SLN did not show any cytotoxic or pro-inflammatory activity in the above described conditions (FIG. 14).

In Vivo Activity of Modified Cyclodextrins

Figure 15:
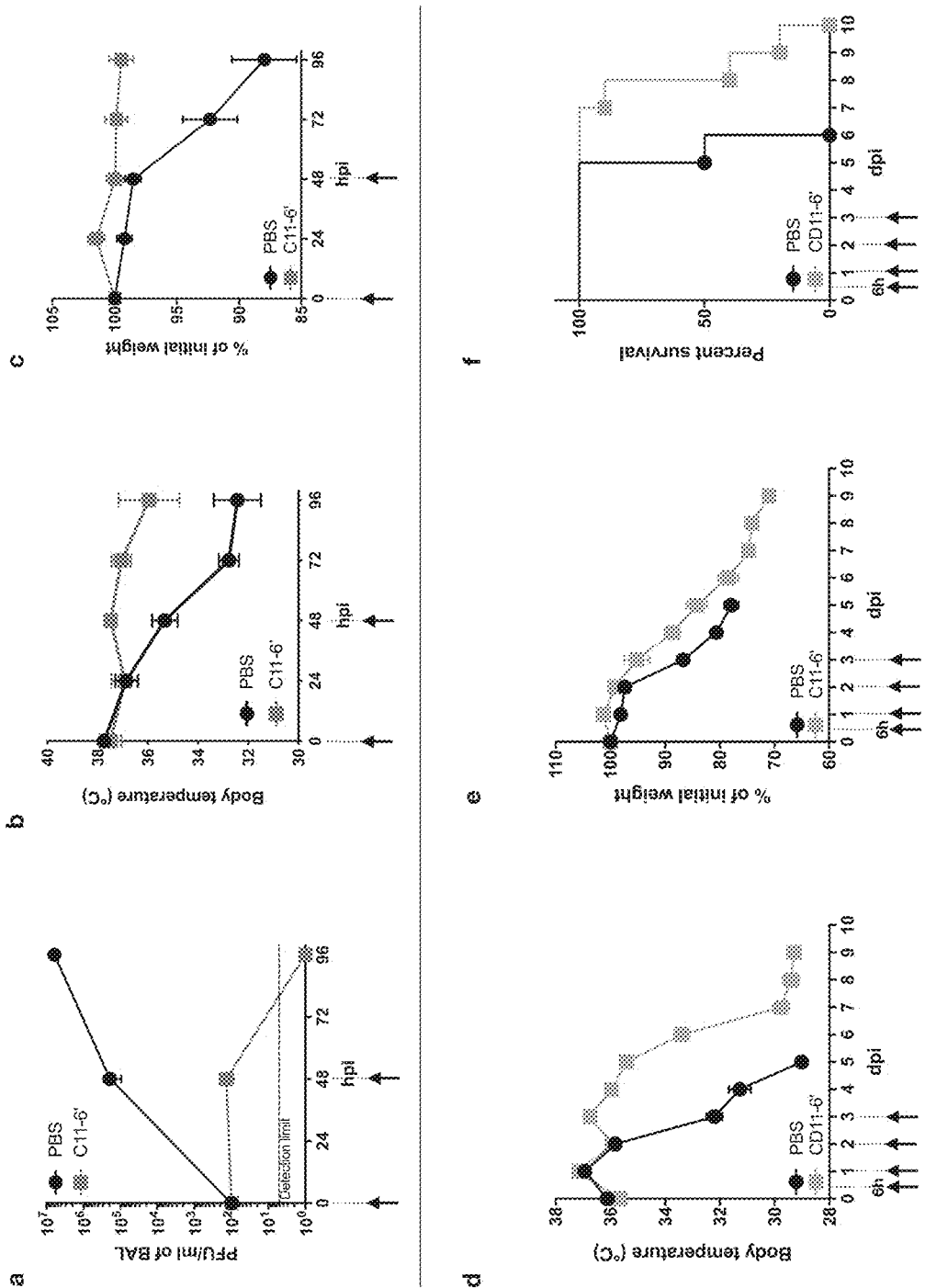
FIG. 15 shows in vivo antiviral activity of C11-6'. (a to c) Mice were intra-nasally treated with PBS or C11-6' simultaneously and 48-hours post-infection with A/NL/09. Viral loads were quantified 48- and 96-hours post-infection (a) and morbidity (loss of temperature (b) and weight (c)) of infected mice was monitored daily. (d to f) Mice were intra-nasally treated with PBS or C11-6' 6-hours post-infection and daily for 3 days (14 µg/mouse). Morbidity (d-e) and survival (f) of infected mice were monitored daily. Results are expressed as means±SEM. Arrows indicate the treatment times.
Figure 16:
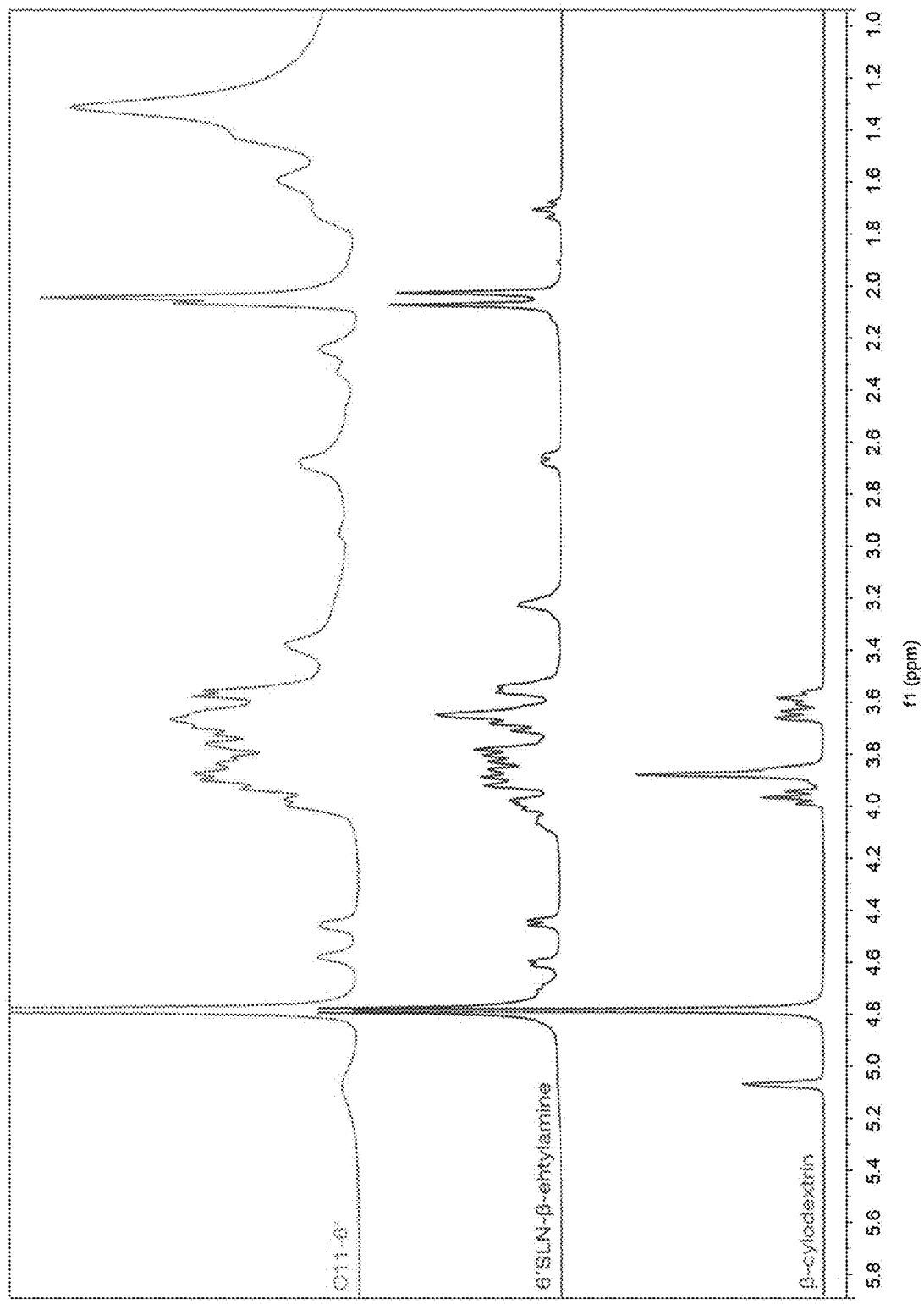
FIG. 16 shows stacked $^1$H NMR spectra of ß-cyclodextrin, 6'SLN-ß-ethylamine and C11-6'.
Figure 17:
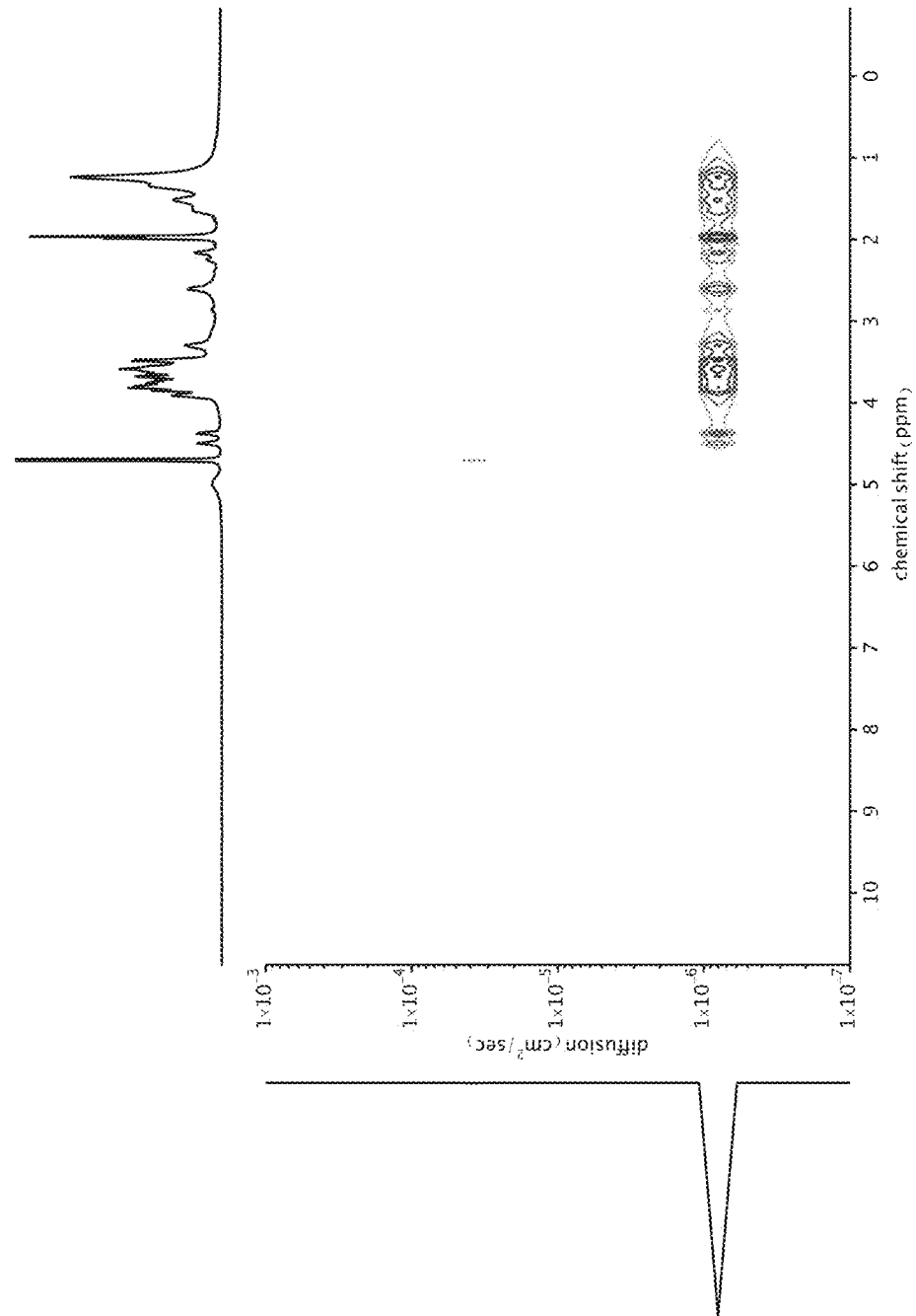
FIG. 17 shows DOSY spectrum of the C11-6' demonstrating that the resulting compound is free from unbound trisaccharides.

In vivo experiments were conducted with BALB/c mice both in co- and post-treatment conditions. In the co-treatment experiments, mice were administered with C11-6'SLN (25 μg/mouse) and A/NL/09 (100 infectious particles/mouse) simultaneously via the intranasal route. The body temperature and the weight of the mice were measured on a daily basis in order to estimate the impact of C11-6'SLN administration on the infected animals' physiological condition. At 2 dpi, half of the mice were randomly euthanized and the rest of the mice retreated with C11-6'SLN. The second group of mice was euthanized at 4 dpi. Viral titers were quantified from broncho-alveolar lavages (BAL) (FIG. 15a). Significant decrease of viral titers was observed at day 2 and 4 post-infection in treated mice (FIG. 15a). The antiviral activity of the C11-6'SLN also significantly diminished morbidity with a significant preservation of both weight and body temperature compared to untreated mice (FIGS. 15b and 15c). Collectively, these results demonstrate the capacity of the C11-6'SLN nanoparticles to prevent in vivo infection and spread of the virus in the lungs.

The in vivo therapeutic potential of C11-6'SLN was also assessed via post-treatment condition. Mice were infected with A/NL/09 (100 infectious particles/mouse) and treated with C11-6'SLN 6 hpi (14 μg/mouse) daily for the next three days with the same dose of nanoparticle (FIGS. 15d to f). Weight and body temperature of the mice were measured each day. Although C11-6'SLN was less potent in the post-treatment condition, it still delayed the progress of the infection. The treated mice displayed a reduction of the morbidity signs (FIGS. 15d and 15e) and better clinical scores. These improvements in the infected-animal's physiological states correlated with prolonged survival (FIG. 15f).

Methods

Synthesis of Modified Cyclodextrins

Chemicals: Neu5Acα(2,6)-Galβ(1-4)-GlcNAc-β-ethylamine and Neu5Acα(2,3)-Galβ(1-4)-GlcNAc-β-ethylamine were purchased from TCI chemicals. Heptakis-(6-deoxy-6-mercapto)-beta-cyclodextrin and carboxymethyl-beta-cyclodextrin sodium salt were purchased from Cyclodextrin-Shop. 11-dodecenoic acid was purchased from abcr GmbH. 14-pentadecenoic acid was purchased from Larodan AB. Maleimide-$PEG_8$-$CH_2CH_2COOH$ was purchased from PurePEG. All the other chemicals and solvents were purchased from Sigma-Aldrich.

Methods: Cyclodextrin derivatives to target influenza virus were synthesized in three steps. The first step was the conjugation of the ligands onto the cyclodextrin. The second step was N-hydroxysuccinimide (NHS) activation of the —COOH end group of the ligands. The third step was SLN grafting onto the ligands.

Step 1: Modification of β-Cyclodextrin with the Ligands 0.04 mmol Heptakis-(6-deoxy-6-mercapto)-beta-cyclodextrin was stirred with 0.28 mmol of bi-functional molecules (ligands) bearing allyl and carboxylic acid end-groups (such as 6-heptenoic acid, 11-dodecenoic acid or 14-pentadecenoic acid) in 5 mL of DMSO, in the presence of a UV lamp (250 W), overnight. The resulting heptakis-(6-deoxy-6-alkanoic acidthion)-beta-cyclodextrin derivatives were precipitated from DCM-diethyl ether mixture by centrifugation and dried under vacuum.

To modify the β-cyclodextrin with the $PEG_8$ spacer, 0.04 mmol heptakis-(6-deoxy-6-mercapto)-beta-cyclodextrin was stirred with 0.28 mmol maleimide-$PEG_8$-$CH_2CH_2COOH$ in the 5 mL of phosphate buffer, pH: 6.8, overnight. The modified β-cyclodextrin was purified with dialysis and dried with lyophilization.

Step 2: NHS Activation Reactions 0.04 mmol of the cyclodextrin derivatives obtained in step 1, respectively, were stirred with 1.12 mmol N-hydroxysuccinimide (NHS), 0.56 mmol ethyl-3-(3-dimethylaminopropyl) carbodiimide (EDC-hcl) and 0.02 mmol 4-dimethylaminopyridine (DMAP) in 5 mL of DMSO, overnight. The resulting NHS-activated cyclodextrin derivatives were firstly precipitated from ice-cold water, and then washed with acetonitrile and diethyl ether. The products were dried under vacuum.

To obtain C1-6', step 1 was skipped and NHS activation reaction was directly conducted. Carboxymethyl-beta-cyclodextrin sodium salt directly (0.04 mmol) was activated with 1.12 mmol NHS 0.56 mmol EDC-hcl and 0.02 mmol DMAP was added. The activation reaction was conducted overnight. The resulting cyclodextrin derivative was first precipitated from a DCM-diethyl ether mixture and further washed three times. The product was dried under vacuum. 6'SLN grafting was conducted in the same way as step 3.

Step 3: Trisaccharide Grafting 5.6 μmol Neu5Acα(2,6)-Galβ(1-4)-GlcNAc-β-ethylamine (Neu5Acα(2,3)-Galβ(1-4)-GlcNAc-β-ethylamine in the case of C11-3') was mixed with 1.6 μmol of the cyclodextrin derivatives obtained in the step 2. 15 μmol triethylamine (TEA) was added and the reaction was conducted overnight in 1 mL DMSO. The reaction products were diluted with 0.01 M phosphate buffer (pH: 7.5) and concentrated using amicon filters (MWCO: 3 k). The resulting heptakis-(6-deoxy-6-SLN-ethylcarboxamido-alkylthio)-beta-cyclodextrin derivatives were further washed with distilled water and dried with lyophilization. The grafting of the trisaccharide onto the ligand-modified cyclodextrins was confirmed with $^1$H and DOSY NMR studies (FIGS. 16 and 17).

Synthesis of C15-6'SLN Modified Cyclodextrin

C15 modification of β-CD: 55 mg of thiol modified β-CD and 70 mg of 14-pentadecenoic acid in 5 mL of DMSO were stirred overnight under UV light.

NHS Activation of C15-β-CD: The resulting material was activated using 100 mg NHS, 75 mg of EDC and 2.5 mg of DMAP in DMF, overnight. NHS-activated C15-β-CD was precipitated from ice-cold water and further washed three times. The last precipitation was done in acetonitrile.

6'SLN grafting onto C15-β-CD: 5 mg C15-β-CD and 5 mg amine functionalized 6'SLN and 3 mg TEA were stirred overnight in DMSO. The resulting material cleaned using amicon filters.

Synthesis of PEG Nanoparticles

Synthesis of PEG(5) NPs: 88.6 mg tetrachloroauric(3) acid trihydrate ($HAuCl_4$*$3H_2O$) in 15 mL of EtOH was mixed with 56 mg of HS-PEG(5) in 5 mL of EtOH for 10 minutes. To the mixture 94.6 mg sodium borohydrate (NaBH4) in 37.5 mL of EtOH was added dropwise. For complete NP formation, an overnight reaction was performed. Resulting NPs were cleaned with amicon filters using EtOH-$H_2O$ solvent mixture.

PEG(5)-C15 mixed ligand NPs: A ligand exchange reaction was performed with 1.5 mg of 16-mercaptohexacanoic acid (HS-C15-COOH) and 20 mg of PEG(5) NPs, in DMF, overnight. The NPs were precipitated from DMF-diethyl ether mixture and further washed three times.

NHS Activation of NPs: 15 mg of NPs were activated using 10 mg N-hydroxysuccinimide ester (NHS), 2 mg of ethylcarbodiimide hydrochloride (EDC) and 0.1 mg of 4-(dimethylamino)-pyridin (DMAP) in DMF, overnight. The resulting NPs were precipitated from DMF-diethyl ether mixture and further washed three times.

6'SLN grafting onto NPs: 5 mg of NHS-activate NPs in 1 mL of DMSO were mixed with 1.7 mg of amine functionalized 6'SLN in 3 mL of 0.1 M phosphate buffer (pH: 7.5). After 5 hours reaction, 6'SLN grafted NPs were cleaned with amicon filters.

Biological Assays

Materials: DMEM—Glutamax medium was purchased from Thermo Fischer Scientific. Tween 20® for washing buffer and 3,3'-diaminobenzidine (DAB) tablets were purchased from Sigma Aldrich. Primary antibody (Influenza A monoclonal antibody) was purchased from Light Diagnostics. Secondary antibody (Anti-mouse IgG, HRP-linked antibody) was purchased from Cell Signaling Technology®. The CellTiter 96® $AQ_{ueous}$ One Solution Cell Proliferation Assay that contains a tetrazolium compound [3-(4,5-dimethylthiazol-2-yl)-5-(3-carboxymethoxyphenyl)-2-(4-sulfophenyl)-2H-tetrazolium, inner salt; MTS] and an electron coupling reagent (phenazine ethosulfate; PES) were purchased from Promega.

Cell Culture:

MDCK (Madin-Darby Canine Kidney Cells) cell line, was purchased from ATCC (American Type Culture Collection, Rockville, MD). The cells were cultured in Dulbecco's modified Eagle's medium with glucose supplement (DMEM+GlutaMAX™) containing 10% fetal bovine serum (FBS) and 1% penicillin/streptomycin. MDCK cell lines was grown in humidified atmosphere with $CO_2$ (5%) at 37° C.

Viral Strains:

A clinical isolate of HSV-2 was originally provided by Prof. M. Pistello, (University of Pisa, Italy) and was propagated and titrated by plaque assay on Vero cells. H1N1 Neth09 and B Yamagata were a kind gift from Prof M. Schmolke (University of Geneva). Avian strain NIBRG-23 (prepared by reverse genetics using A/turkey/Turkey/1/2005 H5N1 surface proteins and A/PR/8/34 (H1N1) backbone) was obtained from National Institute for Biological Standards and Controls, Potters Bar, United Kingdom and was grown further in 10 days old embryonated chicken eggs followed by virus purification and characterization. Clinical samples were provided from the Geneva University Hospital from anonymized patients. All influenza strains were propagated and titrated by ICC on MDCK cells in presence of TPCK-treated trypsin (0.2 mg/ml)

Cell Viability Assays

Cell viability was measured by the MTS [3-(4,5-dimethylthiazol-2-yl)-5-(3-carboxymethoxyphenyl)-2-(4-sulfophenyl)-2H-tetrazolium]assay. Confluent cell cultures seeded in 96-well plates were incubated with different concentrations of nanoparticles or ligand in triplicate under the same experimental conditions described for the antiviral assays. Cell viability was determined by the CellTiter 96 Proliferation Assay Kit (Promega, Madison, WI, USA) according to the manufacturer's instructions. Absorbance was measured using a Microplate Reader (Model 680, BIORAD) at 490 nm. The effect on cell viability at different concentrations of nanoparticles or cyclodextrins was expressed as a percentage, by comparing the absorbance of treated cells with the one of cells incubated with culture medium alone. The 50% cytotoxic concentrations ($CC_{50}$) and 95% confidence intervals (CIs) were determined using Prism software (GraphPad Software, San Diego, CA).

Inhibition Assays

MDCK cells were pre-plated 24 h in advance in 96-well plates. Increasing concentrations of materials were incubated with the influenza virus (MOI: 0.02 or 0.01 for H5N1 and 0.1 for other viruses) at 37° C. for one hour and then the mixtures were added to cells. Following the virus adsorption (1 h at 37° C.), the virus inoculum was removed, the cells were washed and fresh medium was added. After 24 h of incubation at 37° C., the infection was analyzed with immunocytochemical (ICC) assay. The cells were fixed and permeabilized with methanol. Then the primary antibody (1:100 dilution) was added and incubated for 1 hour at 37° C. The cells were washed with wash buffer (DPBS+Tween 0.05%) three times; then secondary antibody (1:750 dilution) was added. After 1 hour the cells were washed and the DAB solution was added. Infected cells were counted and percentages of infection were calculated comparing the number of infected cells in treated and untreated conditions.

In the case of H5N1, flow cytometry-based inhibition assays were conducted additionally. MDCK cells were pre-plated 24 h advanced in 24-well plates (75,000 cells/well). Increasing concentrations of materials were incubated with the influenza virus (MOI: 0.04) at 37° C. for one hour and then the mixtures were added to cells. Following the virus adsorption (1 h at 37° C.), the virus inoculum was removed, the cells were washed and fresh medium was added. After 5 h of incubation at 37° C., the infection was analyzed with flow cytometry. Briefly, cells were trypsinized and fixed using IC fixation buffer (Thermo Fisher Scientific, Netherlands) for 15 minutes at room temperature followed by permeabilization using 1×IC permeabilization buffer (Thermo Fisher Scientific, Netherlands) for 15 minutes at 4° C. Cells were stained with Anti-Influenza A Virus Nucleoprotein mouse monoclonal antibody [D67J](FITC) (Abeam ab210526, The Netherlands) for 30 minutes at 4° C. Antibody dilution was 1:80 in permeabilization buffer and 50 µl per tube was added. FACS analysis was carried out using FACS Calibur 3 software. The concentration producing 50% reduction in the number of infected cells (effective concentration ($EC_{50}$)) was determined using the Prism software. The gating strategy for FACS was performed as shown in FIG. 18. First gating was done based on FSC/SSC and then negative gate for FITC was made. This gating was applied to the remaining samples.

H7N1 infectivity was evaluated through Luciferase activity. MDCK cells were seeded at $5 \times 10^4$ on 96-wells plates. After 24 h, the medium was replaced by serum-free medium. Increasing concentrations of C11-3' were incubated with 100 pfu of H7N1 A/Turkey/Italy/977/1999 encoding the Nanoluciferase. The mixture was incubated 1 h at 37° C. before addition to the cells for another 1 h incubation at 37° C. (100 µL per well). Cells were washed and medium replaced by serum-free medium with 1 µg/mL TPCK-Trypsin. Twenty-four hours post-infection, cells were washed and then lysed with 40 µl per well of Nano Glo® Luciferase Assay Buffer (Promega) diluted ½ in PBS. Luciferase activity was measured in the cell lysates using a Tecan Infinite M200PRO plate reader: 15 µl of Nano Glo® Luciferase Assay Substrate (Promega) diluted 1/5000 in PBS were added to 15 µl of lysate for each well.

Virucidal Assays

Viruses (focus forming unit (ffu):$10^5$/mL) and the test materials ($EC_{99}$ concentration, Table 7) were incubated for 1 hour at 37° C. Serial dilutions of the virus-material complexes together with the non-treated controls were conducted and transferred onto the cells. After 1 hour, the mixture was removed and fresh medium was added. The next day, viral titers were evaluated with ICC assay. For the ICC assay, the same procedure described above was followed.

TABLE 7

The material concentrations at which the in vitro virucidal assays were performed.

| | Material | Concentration (µg/mL) |
|---|---|---|
| A/Netherlands/2009 H1N1 | C6-6' | 100 |
| | C11-6' | 100 |
| | C14-6' | 100 |
| | P8-6' | 500 |
| | C11-3' | 500 |
| | NPs C15-6'SLN | 100 |
| | NPs PEG4-6'SLN | 500 |
| A/Singapore/2004 H3N2 | C11-6' | 100 |
| B/Wisconsin/2010 | C11-6' | 200 |

Data Analysis

All results are presented as the mean values from three independent experiments performed in duplicate. The $EC_{50}$ values for inhibition curves were calculated by regression analysis using the program GraphPad Prism version 5.0

(GraphPad Software, San Diego, California, U.S.A.) to fit a variable slope-sigmoidal dose-response curve.

Ex Vivo

Co-treatment No. 1: H1N1 Neth/09 strain (pfu: $10^4$-$10^5$) and CD-C15-6'SLN (400 ug/mL) were simultaneously added to MucilAir (reconstruction of human airway epithelia). After 4 hours, the supernatant was removed and fresh medium was added. The viral titer of the supernatant was followed every 24 hours with qPCR.

Co-treatment No. 2: Human airway epithelia reconstructed in vitro, MucilAir tissues, (Epithelix Sàrl, Geneva, Switzerland) were cultured at the air-liquid interface from a mixture of nasal polyp epithelial cells originating from healthy donors. Influenza H1N1 pdm 2009 clinical strain (1 e4 rna copies/tissue) and C11-6' (50 μg/tissue) were transferred onto tissues without pre-incubation, together with non-treated control. After 4 hours of incubation time, the tissues were washed twice. On a daily basis, the basal medium was changed. To conduct daily qPCR measurements, 200 uL of medium was added onto tissues and then collected 20 minutes later. RNA extracted with EZNA viral extraction kit (Omega Biotek) was quantified by using qPCR with the QuantiTect kit (#204443; Qiagen, Hilden, Germany) in a StepOne ABI Thermocycler.

Post treatment: MucilAir tissues were infected with H1N1 pdm 2009 (1 e4 copies/tissue). After 4 h the inoculum was removed and tissues were washed. After 20 h an apical wash was done for 20' and subsequently C11-6' (30 μg/tissue), or an equal volume of medium in the untreated tissues, were added apically. Everyday after the 20' apical wash new addition of C11-6' was performed. RNA was then extracted and qPCR done as described above. A similar procedure in the absence of virus was conducted for toxicity studies.

Immunofluorescence

Influenza infected cells were detected by direct with Influenza A antibody (Light Diagnostic) and beta tubulin primary rabbit antibody (Abcam) was used as a marker of ciliated cells. The Alexa 488-goat anti-rabbit Ab and the Alexa 594-goat anti-mouse Ab (Life Technologies) were used as the secondary Ab and nuclei were stained with DAPI. Images were acquired with Zeiss LSM 700 Meta confocal microscope and processed by Imaris.

Lactate Dehydrogenase Assay (LDH)

LDH release in basal medium was measured with the Cytotoxicity Detection Kit (Roche 04744926001).

MTT Assay

MTT solution was diluted in MucilAir medium (1 mg/ml) and 300 μl were added basally in a 24 well plate. After 4 hours incubation at 37° C. the tissues were transferred in new plates and lysed with 1 ml of DMSO. The supernatant was read at 570 nm. Percentages of viability were calculated comparing treated and untreated tissues.

ELISA

Interleukin-6 (IL-6), CXC motif chemokine 10 (CXCL10 or IP-10), CC motif chemokine5 (CCL5 or RANTES), interleukin-8 (IL-8 or CXCL-8) and interferon lambda (IL-29/IL-28B) were measured in the basal medium by ELISA (R&D DY206-05, DY266-05, DY278-05, DY208-05 and DY1598B-05) following everyday treatment with different concentrations of CD.

In Vivo

Pre-treatment: Four groups of five BALB/c mice were treated at day 0 with 50 μl of PBS or C11-6' (25 μg in 50 μl) and immediately inoculated with A/NL/09 ($10^2$ ffu). On a daily basis, body temperature and weight of the mice were measured. Two days post-infection, 2 groups of mice were sacrificed (one group pbs and the other C11-6' treated). Lung homogenate and nasal mucosa and bronchoalveolar lavage were collected to quantify the viral titer through qPCR measurements. The C11-6' treated group was retreated with the same amount of the nanoparticle. Two days after, all the remaining mice were sacrificed, lung homogenate and nasal mucosa were collected. After the tissue disruption, the RNA was extracted with Trizol and quantified by using qPCR while BAL were subjected to plaque assay. Two independent experiments were performed.

Post-treatment: 2 groups of ten BALB/c mice were infected with A/NL/09 ($10^2$ ffu) and treated at 6 hours post infection and subsequently daily for 7 days. Body temperature and weight of the mice were measured daily. Humane endpoint was used during survival study: mice were euthanized via cervical dislocation when body weights were reduced to 75% of the starting weights. In addition, animals that reached moribund state (unresponsive and unaware of stimuli) were also euthanized.

Dose-Response Assays

A fix virus concentration (ffu: $10^3$) was incubated with varying dose of nanoparticles, for 1 hour at 37° C. The mixture then transferred onto cells. After one 1 hour, the mixture was removed and cells were washed. Next day, the infection was analyzed with immunocytochemical (ICC) assay.

REFERENCES

1. Mammen, M., Choi, S. K. & Whitesides, G. M. Polyvalent Interactions in Biological Systems: Implications for Design and Use of Multivalent Ligands and Inhibitors. Angew. Chem. Int. Ed. 37, 2754-2794 (1998).
2. Reuter, J. D. et al. Inhibition of Viral Adhesion and Infection by Sialic-Acid-Conjugated Dendritic Polymers. Bioconjug. Chem. 10, 271-278 (1999).
3. Papp, I. et al. Inhibition of Influenza Virus Infection by Multivalent Sialic-Acid-Functionalized Gold Nanoparticles. Small 6, (2010).
4. Papp, I. et al. Inhibition of Influenza Virus Activity by Multivalent Glycoarchitectures with Matched Sizes. ChemBioChem 12, 887-895 (2011).
5. Tang, S. et al. Antiviral Agents from Multivalent Presentation of Sialyl Oligosaccharides on Brush Polymers. ACS Macro Lett. 5, 413-418 (2016).
6. Kwon, S. J. et al. Nanostructured glycan architecture is important in the inhibition of influenza A virus infection. Nat. Nanotechnol. 12, 48-54 (2017).

The invention claimed is:

1. A virucidal nanoparticle comprising a core and a plurality of ligands covalently linked to the core, wherein at least a portion of said ligands comprise a trisaccharide moiety and wherein:

the core is cyclodextrin wherein the core has a mean diameter of from 1.5 nm to 3 nm, the ligands are the same or different and are hydrophobic optionally substituted $C_4$-$C_{30}$ carboxyalkyl ligands, and each trisaccharide moiety is selected from 3-sialyl-N-acetyllactoseamine (3'SLN) and 6-sialyl-N-acetyllactoseamine (6'SLN), wherein the nanoparticle has a mean particle diameter of from 4.5 nm to 6 nm and wherein said virucidal nanoparticle, following interaction with a virus, irreversibly inhibits infectivity of the virus.

2. The virucidal nanoparticle of claim 1, wherein cyclodextrin is selected from the group consisting of alpha-cyclodextrin, beta-cyclodextrin, and gamma-cyclodextrin.

3. The virucidal nanoparticle of claim 1, wherein the ligands are optionally substituted $C_6$-$C_{15}$ alkyl-based ligand compounds.

4. The virucidal nanoparticle of claim 1, wherein some or all of said ligands comprise 3'SLN, some or all of said ligands comprise 6'SLN, and some but not all of said ligands comprise no trisaccharide moiety.

5. A virucidal nanoparticle represented by Formula (I)

(I)

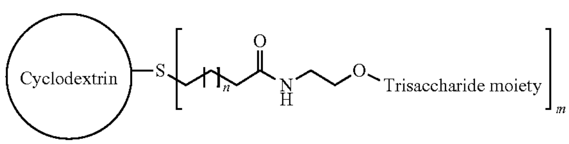

wherein:

m is 1 to 8, n is 4 to 30, the cyclodextrin has a mean diameter of from 1.5 nm to 3 nm and each trisaccharide moiety is selected from 3-sialyl-N-acetyllactoseamine (3'SLN) or 6-sialyl-N-acetyllactoseamine (6'SLN);

wherein the nanoparticle has a mean particle diameter of from 4.5 nm to 6 nm and wherein said virucidal nanoparticle, following interaction with a virus, irreversibly inhibits infectivity of the virus.

6. The virucidal nanoparticle of claim 5, wherein cyclodextrin is selected from the group consisting of alpha-cyclodextrin, beta-cyclodextrin, and gamma-cyclodextrin.

7. The virucidal nanoparticle of claim 5, wherein m is 2, 3 or 4.

8. A virucidal nanoparticle represented by Formula (II)

(II)

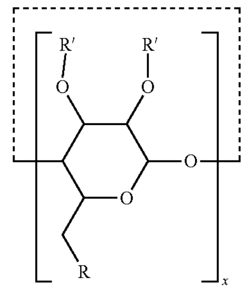

wherein:

each R, independently, is an hydrophobic optionally substituted $C_4$-$C_{30}$ alkyl-based ligand bound by a mercapto group or the corresponding oxygen of the adjacent glucopyranoside unit, wherein at least two of said ligands have a trisaccharide moiety selected from the group consisting of 3-sialyl-N-acetyllactoseamine (3'SLN) and 6-sialyl-N-acetyllactoseamine (6'SLN), or wherein at least one of said ligands has 3'SLN and another has 6'SLN;

each R', independently, is H, $—SO_3^-$, $—SO_4^-$, $—(CH_2)_y—COOH$, $—(CH_2)_y—SO_3^-$, $—(CH_2)_y—SO_4^-$, a polymer or a water solubilizing moiety;

x is 6, 7 or 8; and y is an integer from 4 to 20, or a pharmaceutically acceptable salt thereof, wherein the nanoparticle has a mean particle diameter of from 4.5 nm to 6 nm and wherein said virucidal nanoparticle, following interaction with a virus, irreversibly inhibits infectivity of the virus.

9. The virucidal nanoparticle of claim 8, wherein R' is H.

10. The virucidal nanoparticle of claim 8, wherein said optionally substituted alkyl-based ligands are optionally substituted $C_6$-$C_{15}$ alkyl-based ligands, at least two comprising 6'SLN.

11. The virucidal nanoparticle of claim 5, wherein n is 6 to 15.

12. The virucidal nanoparticle of claim 5, wherein the cyclodextrin further comprises ligands without a trisaccharide moiety wherein the ligands are covalently linked to the cyclodextrin via an —S— group.

* * * * *